(12) United States Patent
Jahnke et al.

(10) Patent No.: US 12,067,895 B2
(45) Date of Patent: Aug. 20, 2024

(54) INK COMPOSITIONS FOR PHANTOMS MIMICKING BIOLOGICAL TISSUE

(71) Applicant: Charité Universitätsmedizin Berlin, Berlin (DE)

(72) Inventors: Paul Jahnke, Berlin (DE); Marco Ziegert, Strausberg (DE); Tetje Henning Dietrich, Berlin (DE); Felix Benjamin Schwarz, Berlin (DE)

(73) Assignee: Charité Universitätsmedizin Berlin, Berlin (DE)

( * ) Notice: Subject to any disclaimer, the term of this patent is extended or adjusted under 35 U.S.C. 154(b) by 880 days.

(21) Appl. No.: 17/046,971

(22) PCT Filed: Apr. 11, 2019

(86) PCT No.: PCT/EP2019/059295
§ 371 (c)(1),
(2) Date: Oct. 12, 2020

(87) PCT Pub. No.: WO2019/201745
PCT Pub. Date: Oct. 24, 2019

(65) Prior Publication Data
US 2021/0049931 A1    Feb. 18, 2021

(30) Foreign Application Priority Data
Apr. 16, 2018  (EP) .................................. 18167576

(51) Int. Cl.
*G09B 23/28*    (2006.01)
*A61B 6/03*    (2006.01)
(Continued)

(52) U.S. Cl.
CPC ............ *G09B 23/286* (2013.01); *A61B 6/032* (2013.01); *A61B 6/583* (2013.01); *A61B 90/39* (2016.02);
(Continued)

(58) Field of Classification Search
CPC ........ A61B 6/032; A61B 6/583; A61N 5/1075
See application file for complete search history.

(56) References Cited

U.S. PATENT DOCUMENTS

2018/0192986 A1* 7/2018 Jahnke ................... G16H 50/50

FOREIGN PATENT DOCUMENTS

EP    3135199 A1    3/2017

OTHER PUBLICATIONS

Berthon, B. et al., A novel phantom technique for evaluating the performance of PET auto-segmentation methods in delineating heterogeneous and irregular lesions, EJNMMI Physics, 2(1)):13, 17 pages, Jun. 27, 2015.
(Continued)

*Primary Examiner* — David P Porta
*Assistant Examiner* — Casey Bryant
(74) *Attorney, Agent, or Firm* — Julie K. Staple; Dinsmore & Shohl LLP

(57) ABSTRACT

The present disclosure relates to the field of imaging phantoms and their use in computed tomography (CT) and radiotherapy (RT). In particular, the present disclosure provides novel ink compositions conferring radiation absorbing properties mimicking biological tissue to imaging phantoms. Thus, these novel ink compositions are particularly useful for creating tissue equivalent imaging phantoms, which allow realistically simulating biological tissue over the whole range of photon energies relevant for applications in CT and RT. Accordingly, the present disclosure also provides novel imaging phantoms exhibiting radiation absorbing properties mimicking real biological tissue. The present disclosure further relates to methods of generating imaging phantoms built up of layers making use of the novel ink compositions disclosed herein.

13 Claims, 6 Drawing Sheets

(51) Int. Cl.
A61B 6/58 (2024.01)
A61B 90/00 (2016.01)
A61N 5/10 (2006.01)
C09D 11/03 (2014.01)

(52) U.S. Cl.
CPC ............ *A61N 5/1075* (2013.01); *C09D 11/03* (2013.01); *A61B 2090/3966* (2016.02); *A61N 2005/1076* (2013.01)

(56) References Cited

OTHER PUBLICATIONS

De Gans, B.-J. et al., Inkjet Printing of Polymer Micro-Arrays and Libraries: Instrumentation, Requirements, and Perspectives, Macromolecular Rapid Communications, 24(11): 659-666, Jul. 7, 2003.

\* cited by examiner

FIGURE 1: Photon energy range in computed tomography (CT) and radiotherapy (RT)
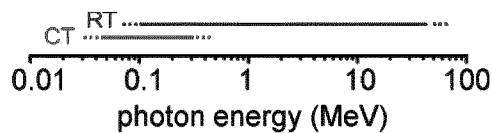
FIGURE 2: Mass attenuation coefficients of oxygen, calcium and iodine
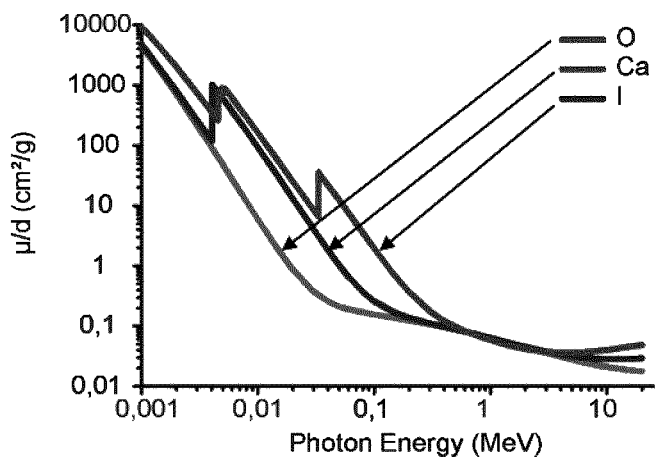
FIGURE 3: CT values of different human tissues
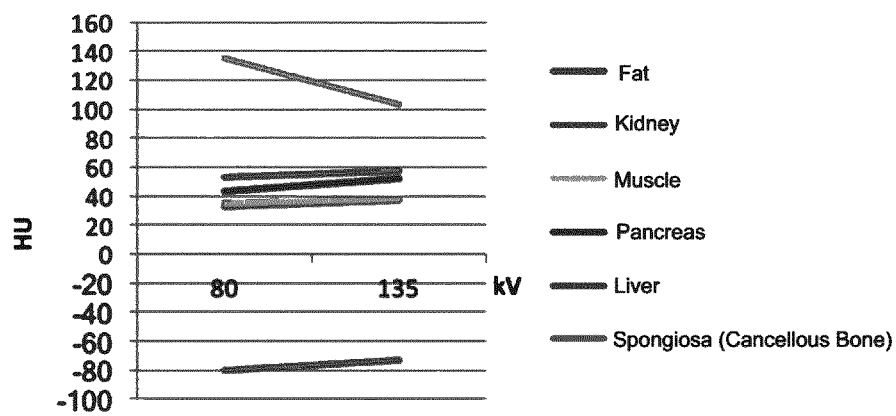

FIGURE 4: Exemplary manufacturing process of patient-individual phantom.
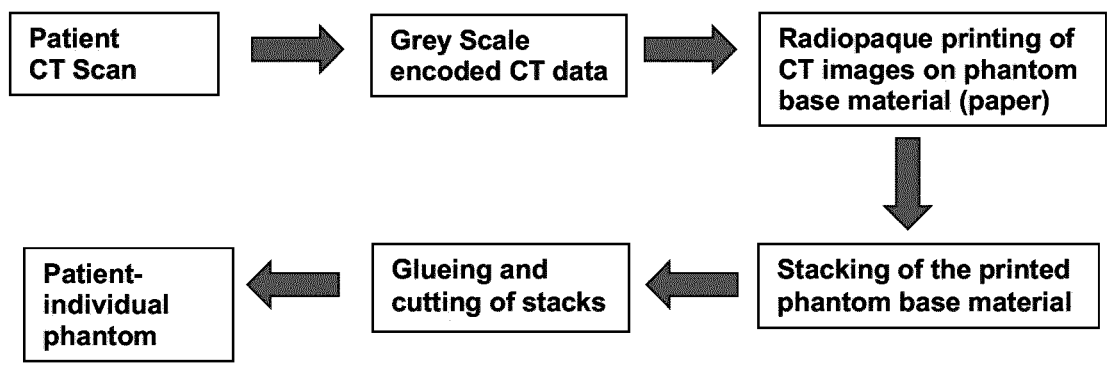
FIGURE 5: Mass attenuation coefficient (left) and CT values (right) of the phantom base material
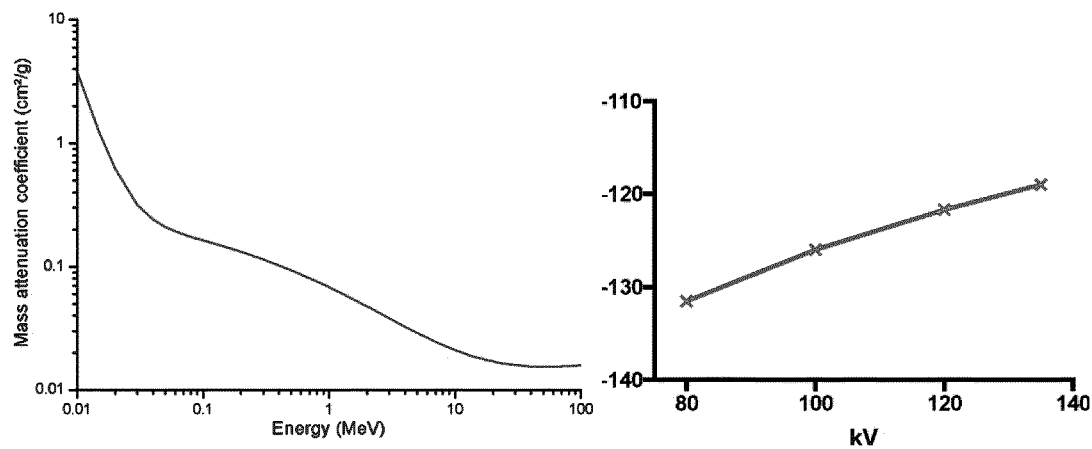

FIGURE 6: Mass attenuation coefficients of skeletal muscle tissue and phantom (top; graphs are overlapping), and ratio of mass attenuation coefficients (bottom)
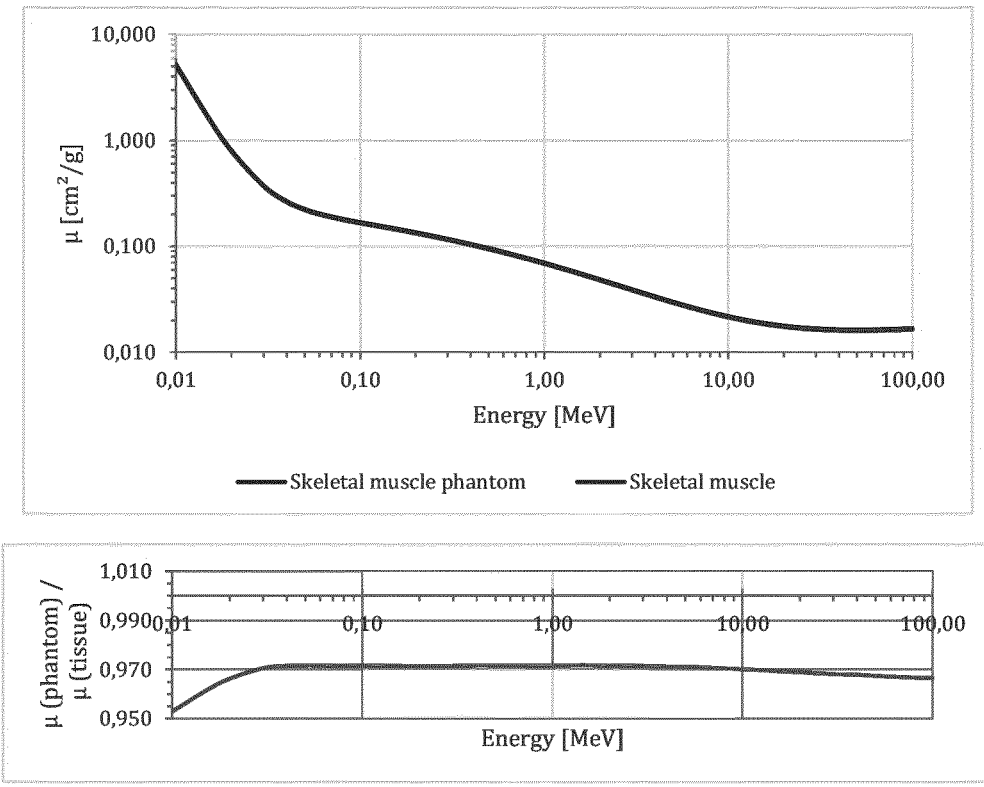
FIGURE 7: Mass attenuation coefficients of cortical bone tissue and phantom (top; graphs are overlapping) and ratio of mass attenuation coefficients (bottom).
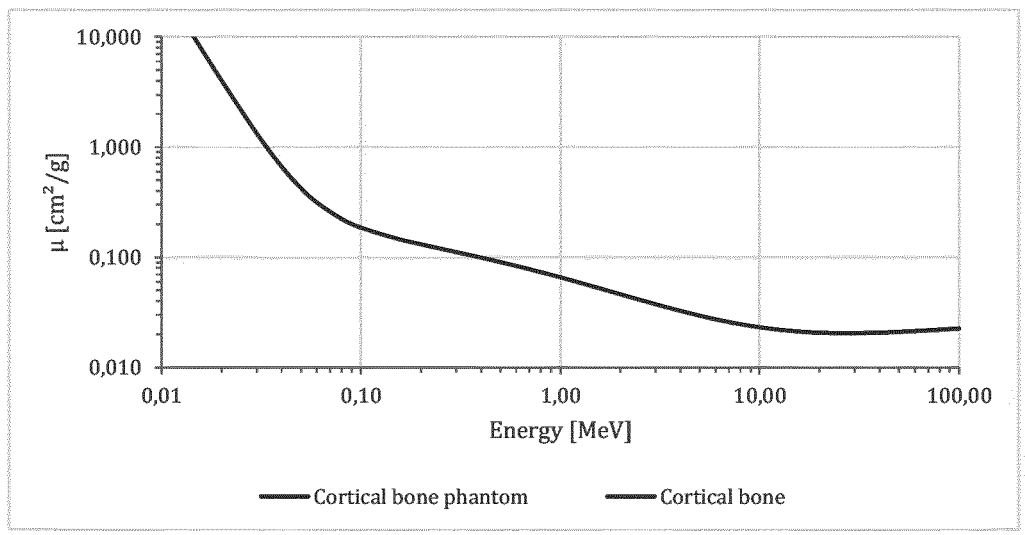

FIGURE 8: Table showing mass attenuation coefficients and density values of phantoms and reference materials.

| Energy [MeV] | μ Phantom base material | μ Skeletal muscle | μ Skeletal muscle phantom | μ Cortical bone | μ Cortical bone phantom |
|---|---|---|---|---|---|
| 0.01 | 3.85022 | 5.25856 | 5.01100 | 28.51580 | 28.81808 |
| 0.02 | 1.24211 | 1.66479 | 1.60045 | 9.03134 | 9.09763 |
| 0.02 | 0.62859 | 0.80877 | 0.78146 | 4.00110 | 4.01794 |
| 0.03 | 0.31877 | 0.37479 | 0.36374 | 1.33091 | 1.33153 |
| 0.04 | 0.24082 | 0.26696 | 0.25935 | 0.66546 | 0.66478 |
| 0.05 | 0.20987 | 0.22540 | 0.21901 | 0.42413 | 0.42349 |
| 0.06 | 0.19334 | 0.20416 | 0.19837 | 0.31481 | 0.31426 |
| 0.08 | 0.17500 | 0.18198 | 0.17679 | 0.22291 | 0.22270 |
| 0.10 | 0.16357 | 0.16903 | 0.16423 | 0.18553 | 0.18548 |
| 0.15 | 0.14491 | 0.14902 | 0.14476 | 0.14806 | 0.14811 |
| 0.20 | 0.13207 | 0.13564 | 0.13176 | 0.13089 | 0.13098 |
| 0.30 | 0.11446 | 0.11745 | 0.11410 | 0.11135 | 0.11144 |
| 0.40 | 0.10244 | 0.10507 | 0.10209 | 0.09908 | 0.09917 |
| 0.50 | 0.09351 | 0.09590 | 0.09318 | 0.09023 | 0.09030 |
| 0.60 | 0.08646 | 0.08866 | 0.08615 | 0.08332 | 0.08339 |
| 0.80 | 0.07593 | 0.07787 | 0.07565 | 0.07308 | 0.07315 |
| 1.00 | 0.06827 | 0.07001 | 0.06801 | 0.06566 | 0.06572 |
| 1.02 | 0.06755 | 0.06927 | 0.06730 | 0.06497 | 0.06503 |
| 1.25 | 0.06104 | 0.06259 | 0.06082 | 0.05871 | 0.05876 |
| 1.50 | 0.05555 | 0.05696 | 0.05535 | 0.05346 | 0.05351 |
| 2.00 | 0.04768 | 0.04891 | 0.04752 | 0.04607 | 0.04611 |
| 2.04 | 0.04711 | 0.04833 | 0.04695 | 0.04554 | 0.04559 |
| 3.00 | 0.03825 | 0.03927 | 0.03815 | 0.03745 | 0.03747 |
| 4.00 | 0.03274 | 0.03365 | 0.03268 | 0.03257 | 0.03258 |
| 5.00 | 0.02911 | 0.02996 | 0.02909 | 0.02946 | 0.02946 |
| 6.00 | 0.02656 | 0.02736 | 0.02656 | 0.02734 | 0.02733 |
| 7.00 | 0.02466 | 0.02544 | 0.02469 | 0.02581 | 0.02580 |

| 8.00 | 0.02320 | 0.02396 | 0.02326 | 0.02467 | 0.02466 |
|---|---|---|---|---|---|
| 9.00 | 0.02206 | 0.02281 | 0.02213 | 0.02381 | 0.02379 |
| 10.00 | 0.02113 | 0.02187 | 0.02122 | 0.02314 | 0.02312 |
| 11.00 | 0.02037 | 0.02111 | 0.02047 | 0.02261 | 0.02258 |
| 12.00 | 0.01973 | 0.02047 | 0.01985 | 0.02218 | 0.02214 |
| 13.00 | 0.01920 | 0.01993 | 0.01933 | 0.02183 | 0.02180 |
| 14.00 | 0.01875 | 0.01948 | 0.01889 | 0.02155 | 0.02151 |
| 15.00 | 0.01836 | 0.01909 | 0.01851 | 0.02132 | 0.02128 |
| 16.00 | 0.01803 | 0.01876 | 0.01819 | 0.02114 | 0.02110 |
| 18.00 | 0.01748 | 0.01822 | 0.01765 | 0.02086 | 0.02081 |
| 20.00 | 0.01706 | 0.01780 | 0.01725 | 0.02068 | 0.02063 |
| 22.00 | 0.01674 | 0.01749 | 0.01694 | 0.02057 | 0.02052 |
| 24.00 | 0.01648 | 0.01724 | 0.01670 | 0.02051 | 0.02045 |
| 26.00 | 0.01627 | 0.01704 | 0.01650 | 0.02047 | 0.02041 |
| 28.00 | 0.01612 | 0.01688 | 0.01635 | 0.02047 | 0.02041 |
| 30.00 | 0.01598 | 0.01676 | 0.01622 | 0.02049 | 0.02042 |
| 40.00 | 0.01562 | 0.01643 | 0.01590 | 0.02072 | 0.02064 |
| 50.00 | 0.01552 | 0.01636 | 0.01583 | 0.02105 | 0.02098 |
| 60.00 | 0.01554 | 0.01640 | 0.01586 | 0.02140 | 0.02132 |
| 80.00 | 0.01570 | 0.01660 | 0.01605 | 0.02205 | 0.02194 |
| 100.00 | 0.01590 | 0.01684 | 0.01628 | 0.02259 | 0.02248 |
| Physical Density | 0.9 | 1.05 | 1.05 | 1.92 | 1.92 |

FIGURE 9: Exemplary head phantom of a patient comprising stacks of multiple paper layers

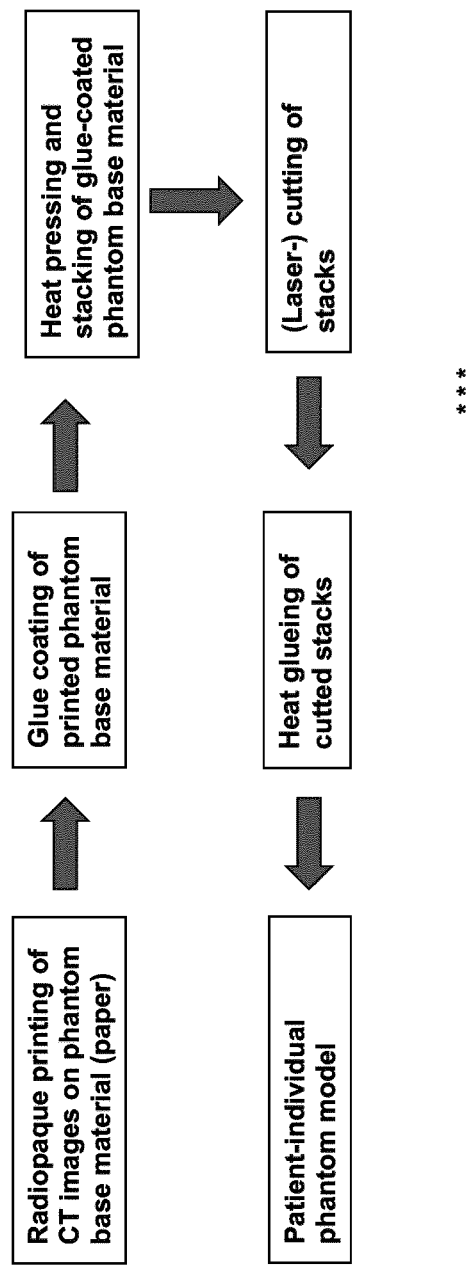
FIGURE 10: Novel phantom manufacturing process provided by the present disclosure (exemplified).

INK COMPOSITIONS FOR PHANTOMS MIMICKING BIOLOGICAL TISSUE

TECHNICAL FIELD

The present disclosure relates to the field of phantoms, in particular anthropomorphic phantoms, and their use in computed tomography (CT) and radiotherapy (RT). In particular, the present disclosure relates to novel ink compositions conferring radiation absorbing properties mimicking biological tissue to phantoms, in particular anthropomorphic phantoms. The present disclosure also relates to methods of generating phantoms built up of layers making use of the novel ink compositions disclosed herein.

TECHNICAL BACKGROUND

Phantoms are widely used in computed tomography (CT) and radiotherapy (RT). However, it is considered that exposure of individual patients to ionizing radiation cannot be simulated realistically with commonly used geometric phantoms.

In order to more realistically represent the human (or animal) body (or parts thereof), the design of anthropomorphic phantoms has been the subject of investigation. Alderson et al. (*Am J Roentgenol Radium Ther Nucl Med* 1962, 87, 185-195) have developed an anthropomorphic phantom, which is known as the Alderson phantom (RSD, Long Beach, Calif.), and which is composed of a limited number of tissue-simulating materials including bone, lung and soft tissue, with an average human shape. The manufacture of traditional anthropomorphic phantoms such as Alderson-type anthropomorphic phantoms is complex and time-consuming. Such phantoms may provide for approximation of radiation attenuation of the body of an individual patient, however, they are limited as regards a more detailed simulation of human tissue characteristics.

There was a need for phantoms that realistically mimic both anatomy and radiation absorption characteristics of the human (or animal) body. The processing of data sets from CT or MRI scans allows the generation of printable 3D computer models. Phantoms that are based on 3D printing applying different technologies have been described (E. D. Ehler et al., *Phys Med Biol* 2014, 59, 5763-5773; J. Ceh et al., *Sensors* (Basel) 2017, 17; R. Mayer et al. *Rev Sci Instrum* 2015, 86, 074301; J. I. Gear et al., *Med Phys* 2014, 41, 082502; C. N. Ionita et al., *Proc SPIE Int Soc Opt Eng* 2014, 9038, 90380M; J. Jung et al., *Int J Radiat Oncol Biol Phys* 2015, 92, 745-753; N. Kiarashi et al., *Med Phys* 2015, 42, 4116-4126; M. J. Kim et al., *PLoS One* 2017, 12, e0176227; M. Leary et al., *Materials & Design* 2015, 86, 487-499; J. Madamesila et al., *Phys Med* 2016, 32, 242-247). For example, a 3D printed head phantom for dosimetric measurements in radiation therapy printed with a fused deposition modeling (FDM) 3D printer has been generated by Ehler et al. (2014). Furthermore, thorax phantom distinguishing soft and bone tissue has been generated by Mayer et al. (2015) using a multi-material Poly Jet 3D printer combining materials with different absorption characteristics.

These 3D printing technologies provide ready-to-use technology for 3D printing of individual phantoms, however, they were not developed with the aim of printing 3D models for simulating radiation attenuation of individual patients. For instance, the use of FDM 3D printers only allows the generation of homogeneous objects, which means that they cannot be used for the manufacture of advanced phantoms. The reported 3D printing technologies provide phantoms that are considered to significantly deviate from the individual patient as regards radiation attenuation characteristics, and also represent rather complex and expensive technologies, like the advanced photopolymerization printers.

Jahnke et al. (*Radiology* 2016, 282(2), 152710) describe a 3D printing method that specifically allows the generation of anthropomorphic phantoms exhibiting radiation attenuation properties of individual patients. In particular, using inkjet technology, medical images obtained from patient individual CT scans were printed on paper sheets, which upon stacking and cutting result in three-dimensional phantom models showing defined radiation attenuation properties, thereby demonstrating the feasibility of anatomy representation and HU equivalence. Tissue equivalence describes the realistic simulation of radiation absorption properties of human tissue over the energy range relevant for CT and RT. The present disclosure particularly addresses this object and provides novel ink compositions for phantoms mimicking human tissue realistically with respect to both anatomy and radiation absorption characteristics of individual patients.

SUMMARY OF THE INVENTION

The present disclosure provides novel ink compositions conferring radiation absorbing properties mimicking biological tissue. These novel ink compositions are particularly useful for creating tissue equivalent anthropomorphic phantoms. Accordingly, the present disclosure provides novel phantoms, in particular novel anthropomorphic phantoms, exhibiting radiation absorbing properties mimicking real biological tissue. These novel phantoms allow realistically simulating biological tissue, including both biological soft tissue and bone tissue, over the whole range of photon energies relevant for applications in computed tomography (CT) and radiotherapy (RT). The novel anthropomorphic phantoms provided by the present disclosure are particularly useful for dosimetric measurements in radiotherapy. Phantoms provided by the present disclosure feature Hounsfield units close to or corresponding to biological equivalents. They allow repeated imaging of specific body regions, in different settings without the danger of harming a subject.

In particular, the present disclosure provides:

[1] Ink composition conferring radiation absorbing properties mimicking biological tissue, wherein the composition comprises dissolved radiation absorbing molecules composed of chemical elements having: (a) a low-atomic number $1 \leq Z \leq 11$, preferably a low-atomic number $1 \leq Z \leq 8$; and/or (b) an atomic number in the range $Z=12-22$, preferably in the range $Z=15-20$.

[2] Ink composition conferring radiation absorbing properties mimicking biological soft tissue, wherein the ink composition comprises radiation absorbing organic molecules and/or salts selected from any of: (i) sugars and derivatives thereof, preferably aldoses including glucose and mannose, ketoses including fructose, disaccharides including lactose, maltose and saccharose, sugar alcohols including sorbitole, and/or amino sugars including meglumin; (ii) pyridine-, pyrimidine-, purine-, imidazole-, pyrazole-, and/or indole derivatives; (iii) amino acids and derivatives thereof, preferably proline and lysine; (iv) carboxylic acids and derivatives thereof, preferably citric acid, tartaric acid, and/or amides including urea and caprolactam; (v) polymers having a low molecular weight≤30 kDa; and/or (vi) ammonium-, lithium-, sodium- and/or magnesium-salts, wherein the radiation absorbing organic molecules and/or salts according to any of (i) to (vi) are water-soluble, non-volatile compounds having a boiling point≥200° C., and wherein the ink composition has a viscosity in the range between 1-30 mPa·s, preferably in the range between 2-15 mPa·s.

[3] Ink composition conferring radiation absorbing properties mimicking biological bone tissue, wherein the ink composition comprises radiation absorbing salts selected from any of: (i) sodium, magnesium, aluminum salts; (ii) potassium salts, preferably potassium-chloride, -phosphate, -sulfate, -thiosulfate, -thiocyanate, and/or -diphosphate; (iii) calcium salts, preferably calcium chloride and nitrate; (iv) scandium salts; (v) titanium-salts; (vi) phosphates including di-, tri-, and poly-phosphates, hydrogenphosphates, dihydrogenphosphates, mono-, di-, tri-, and tetra-thiophosphates; phosphonates, phosphinates, (vii) sulfates including hydrogensulfates and thiosulfates; sulfites including hydrogensulfites, sulfides including hydrogensulfides, thiocyanates, isothiocyanates, di- and polythionates, (xiii) chlorides; (ix) chlorates; (x) perchlorates, and/or (xi) silicates; wherein the radiation absorbing salts according to any of (i) to (xi) are water-soluble, non-volatile compounds having a boiling point≥200° C., and wherein the ink composition has a viscosity in the range between 1-30 mPa·s, preferably in the range between 2-15 mPa·s.

[4] The ink composition of [1] or [2], wherein the radiation absorbing molecules and/or salts composed of elements having a low-atomic number $1 \leq Z \leq 11$ are present in the composition in an amount of at least 75% w/w, preferably at least 80% w/w, relative to the total dry weight of the dissolved radiation absorbing molecules and/or radiation absorbing salts.

[5] The ink composition of [4], wherein the remaining amount of 25% w/w or less, or 20% w/w or less, respectively, relative to the total dry weight of the dissolved radiation absorbing molecules comprise radiation absorbing molecules and/or radiation absorbing salts, composed of elements having an atomic number in the range $Z=12$-$22$, and/or wherein the amount of radiation absorbing molecules and/or radiation absorbing salts composed of elements having an atomic number $Z>22$ present in the composition does not exceed 1% w/w relative to the total dry weight of the dissolved radiation absorbing molecules and/or radiation absorbing salts.

[6] The ink composition of [1] or [3], wherein the radiation absorbing molecules and/or salts composed of elements having an atomic number in the range $Z=12$-$22$ are present in the composition in an amount of at least 50% w/w, preferably 70% w/w, relative to the total dry weight of the dissolved radiation absorbing molecules and/or radiation absorbing salts.

[7] The ink composition of [6], wherein the remaining amount of 50% w/w or less, or 30% w/w or less, respectively, relative to the total dry weight of the dissolved radiation absorbing molecules and/or radiation absorbing salts, comprise radiation absorbing molecules composed of elements having an atomic number low-atomic number $1 \leq Z \leq 11$, and/or wherein the amount of radiation absorbing molecules and/or radiation absorbing salts composed of elements having an atomic number $Z>22$ present in the composition does not exceed 5% w/w relative to the total dry weight of the dissolved radiation absorbing molecules and/or radiation absorbing salts.

[8] The ink composition of any one of [1]-[7], wherein the radiation absorbing molecules confer to a phantom/an imaging phantom, which is generated with the ink composition, a mass attenuation coefficient $\mu/\rho$ value≤0.2 cm²/g at 100 keV, preferably in the range of 0.160-0.195 cm²/g at 100 keV.

[9] Use of the ink composition according to any one of [1] to [8] for generating a phantom/an imaging phantom.

[10] A phantom, in particular an anthropomorphic phantom, exhibiting radiation absorbing properties mimicking biological tissue at a photon energy (or at at least one, or one or more photon energies) in the range of 20 keV to 100 MeV (or 20 keV to 50 MeV), wherein the phantom is built up of layers carrying (i) the radiation absorbing molecules of the ink composition according to [1], (ii) the radiation absorbing organic molecules and/or salts of the ink composition according to [2]; and/or (iii) the radiation absorbing salts of the ink composition according to [3]. The present disclosure encompasses the use of the imaging phantoms provided herein in computed tomography (CT) and radiotherapy (RT). Accordingly, in various embodiments of the present disclosure, the novel imaging phantoms disclosed herein may be considered as CT and/or RT (imaging) phantoms. The terms computed tomography and computer tomography may be used herein interchangeably.

[11] The phantom according to [10], wherein the phantom shows a mass attenuation coefficient $\mu/\rho$ value≤0.2 cm²/g at 100 keV, preferably in the range of 0.160-0.195 cm²/g at 100 keV.

[12] The phantom according to [10] or [11], wherein the phantom: (i) is mimicking the radiation absorbing properties of biological soft tissue; and/or has a Hounsfield Unit (HU) value between −200 and +300 in a CT scan with a tube voltage of 120 kV; (ii) is mimicking the radiation absorbing properties of biological bone tissue, preferably of cortical bone tissue; and/or has a Hounsfield Unit (HU) value between −50 and +3000 in a CT scan with a tube voltage of 120 kV.

[13] A method of generating a phantom/an imaging phantom, in particular an anthropomorphic phantom, exhibiting radiation absorbing properties mimicking biological tissue, wherein the method comprises a step of printing the ink composition according to any of [1] to [8] onto multiple layers.

[14] The method of [13], further comprising generating stacks of multiple layers, preferably wherein each stack comprises at least two layers and has a thickness of at least 80 µm, preferably wherein each stack comprises at least 10 layers and has a thickness of at least 400 µm, more preferably wherein each stack comprises at least 50 layers and has a thickness of at least 2 mm.

[15] The (imaging) phantom according to any one of [10]-[12], or the method according to [13] or [14], wherein the layer has a thickness of at least 40 µm, and/or comprises pulp material, preferably cellulose, and/or comprises a thermoplastic coating, preferably a polyethylene coating, on one side of its surface.

[16] As described herein, in various embodiments of the present disclosure, including any of the above [1] to [15], the biological (soft/bone) tissue preferably is a mammalian (soft/bone) tissue, including both human and animal (soft/bone) tissue. More preferably, the biological (soft/bone) tissue is a human (soft/bone) tissue.

[17] As described herein, in various embodiments of the present disclosure, including any of the above [1] to [16], the terms "imaging phantom", "phantom", "imaging model", and "phantom model" may be used interchangeably. The term "phantom" or "imaging phantom" encompasses both "anthropomorphic phantoms" and "animal phantoms". In preferred embodiments, the "phantom" or "imaging phantom" is an "anthropomorphic phantom". Accordingly, in preferred embodiments, the "phantom" or "imaging phantom" is an "anthropomorphic phantom", and the biological (soft/bone) tissue is human (soft/bone) tissue.

BRIEF DESCRIPTION OF THE DRAWINGS

FIG. 1: shows the photon energy range in Computed tomography (CT) and Radiotherapy (RT)

FIG. 2: shows mass attenuation coefficients of oxygen, calcium and iodine. O=bottom graph; Ca=mid graph; I=upper graph.

FIG. 3: shows CT values of different human tissues with increasing photon energy from 80-135 keV. Graphs from top to bottom: spongiosa (cancellous bone), liver, pancreas, muscle and kidney (graphs nearly overlapping), and fat.

FIG. 4: shows an exemplary manufacturing process of a patient-individual phantom.

FIG. 5: shows mass attenuation coefficient (left) and CT values (right) of phantom base material.

FIG. 6: shows mass attenuation coefficients of skeletal muscle tissue and phantom (top), and ratio of mass attenuation coefficients (bottom).

FIG. 9: shows an example of a head phantom of a patient comprising stacks of multiple paper layers, manufactured according to the methods disclosed herein.

FIG. 10: shows a novel phantom manufacturing process provided by the present disclosure (exemplified).

DETAILED DESCRIPTION OF THE INVENTION

Figure 7:
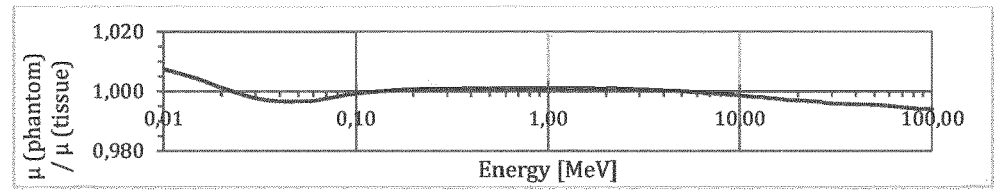
FIG. 7: shows mass attenuation coefficients of cortical bone tissue and phantom (top) and ratio of mass attenuation coefficients (bottom).

The present inventors developed an easy to use, universally applicable and inexpensive printing method specifically designed for creating phantoms, in particular anthropomorphic phantoms, with the anatomy and attenuation properties of individual subjects and/or tissues. Using conventional inkjet technology and specifically formulated novel ink compositions, medical images were printed on paper sheets. Stacking, gluing and cutting these sheets gives three-dimensional objects with defined radiation absorption properties of individual patients. The development process was advanced in three major steps: anatomy representation, HU equivalence and tissue equivalence, wherein the third development step, tissue equivalence, describes the realistic simulation of the radiation absorption properties of biological tissue over the energy range relevant for CT and RT. The feasibility in particular of the third parameter has been successfully demonstrated in the present disclosure based on the specifically formulated novel ink compositions provided herein.

In particular, the present disclosure provides a novel ink composition conferring radiation absorbing properties mimicking biological tissue, wherein the composition comprises dissolved radiation absorbing molecules composed of chemical elements having (a) a low-atomic number $1 \leq Z \leq 11$, preferably a low-atomic number $1 \leq Z \leq 8$; and/or (b) an atomic number in the range $Z=12-22$, preferably in the range $Z=15-20$.

In various embodiments, the radiation absorbing molecules composed of chemical elements having a low-atomic number $1 \leq Z \leq 11$, preferably a low-atomic number $1 \leq Z \leq 8$, are molecules composed of elements including C, N, H and/or O.

Furthermore, in various embodiments, the radiation absorbing molecules composed of chemical elements having an atomic number in the range $Z=12-22$, preferably in the range $Z=15-20$, are molecules are composed of elements including S, Cl, P, Ca, and/or K.

Soft tissues such as muscles or organs are similarly composed of elements with a low atomic number, but have compared to, e.g., adipose tissue a higher oxygen and a lower carbon content (See Table 1 in the section "Examples"). While adipose tissue is mostly composed of elements with a low atomic number and has a density in the range of 0.9-0.97 g/cm$^3$, the physical density of soft tissue is in the range of 1.0-1.1 g/cm$^3$. Bone tissue contains besides low atomic number elements a significant amount of phosphorus and calcium and has density values of up to 1.92 g/cm$^3$. In various embodiments of the present invention, a novel ink composition according to the present disclosure comprises dissolved radiation absorbing molecules composed of elements having a low-atomic number $1 \leq Z \leq 11$, wherein the ratio of the elements O:C is at least about 3:1, preferably at least about 4:1, among the said elements having a low-atomic number $1 \leq Z \leq 11$. Preferably, the elemental composition of the radiation absorbing molecules is characterized by a phosphorus content (w % or % w/w) of less than 10% w/w, preferably less than 5% w/w, more preferably less than 3% w/w, and even more preferably less than 1% w/w relative to the dry weight of the dissolved radiation absorbing molecules. More preferably, the elemental composition of the radiation absorbing molecules is further characterized by a calcium content (% w/w or w/%) of less than 10% w/w, preferably less than 5% w/w, more preferably less than 3% w/w, and even more preferably less than 1% w/w relative to the dry weight of the dissolved radiation absorbing molecules.

In various embodiments of the present disclosure, a novel ink composition according to the present disclosure comprises dissolved radiation absorbing molecules composed of elements having an atomic number $Z=12-22$, wherein the ratio of the elements O:C is less than about 4:1 among the said elements having an atomic number $Z=12-22$. Preferably, the elemental composition of the radiation absorbing molecules is characterized by a phosphorus content (% w/w or w/%) of more than 1% w/w, preferably more than 3% w/w, more preferably more than 5% w/w, and even more preferably more than 10% w/w relative to the dry weight of the dissolved radiation absorbing molecules. More preferably, the elemental composition of the radiation absorbing molecules is further characterized by a calcium content (% w/w or w/%) of more than 1% w/w, preferably more than 3% w/w, more preferably more than 5% w/w, and even more preferably more than 10% w/w relative to the dry weight of the dissolved radiation absorbing molecules.

In various preferred embodiments, the elemental composition of the molecules is characterized by 4-6% w/w H, 22-24% w/w C, 25-27% w/w N, and/or 22-24% w/w O. In various embodiments, the elemental composition of the molecules is further characterized by 7-9% w/w Na, and/or 12-14% w/w Cl. Still further, the elemental composition of the molecules may be characterized by 0.1-0.5% w/w S. Ink compositions comprising molecules having the aforementioned elemental composition(s) are particularly useful as "skeletal muscle inks". In particularly preferred embodiments, the elemental composition of the molecules is characterized by 5.4% w/w H, 23.1% w/w C, 26.5% w/w N, and/or 23.0% w/w O. In various embodiments, the elemental composition of the molecules is further characterized by 8.6% w/w Na, and/or 13.3% w/w Cl. Still further, the elemental composition of the molecules may be characterized by 0.1% w/w S.

In various preferred embodiments, the elemental composition of the molecules is characterized by 1-3% w/w H, 12-14% w/w C, 1-2% w/w N, and/or 11-13% w/w O. In various embodiments, the elemental composition of these molecules is further characterized by 33-35% w/w Cl, and/or 37-39% w/w K. Still further, the elemental composition of these molecules may be characterized by 0.1-0.5% w/w S. Ink compositions comprising molecules having the aforementioned elemental composition(s) are particularly useful as "cortical bone inks". In particularly preferred embodiments, the elemental composition of the molecules is characterized by 1.9% w/w H, 12.8% w/w C, 1.3% w/w N, and/or 11.7% w/w O. In various embodiments, the elemental composition of these molecules is further characterized by 34.3% w/w Cl, and/or 37.9% w/w K. Still further, the elemental composition of these molecules may be characterized by 0.1% w/w S.

In various embodiments of the present disclosure, the radiation absorbing (organic) molecules composed of chemical elements having (a) a low-atomic number $1 \leq Z \leq 11$, preferably a low-atomic number $1 \leq Z \leq 8$; and/or (b) an atomic number in the range $Z=12-22$, preferably in the range $Z=15-20$ are non-volatile radiation absorbing (organic) molecules composed of chemical elements having (a) a low-atomic number $1 \leq Z \leq 11$, preferably a low-atomic number $1 \leq Z \leq 8$; and/or (b) an atomic number in the range $Z=12-22$, preferably in the range $Z=15-20$. Preferably, the said non-volatile radiation absorbing (organic) molecules are water-soluble, non-volatile radiation absorbing (organic) molecules or compounds having a boiling point$\geq 200°$ C.

In various embodiments, the radiation absorbing molecules composed of chemical elements having (a) a low-atomic number $1 \leq Z \leq 11$, preferably a low-atomic number $1 \leq Z \leq 8$; and/or (b) an atomic number in the range $Z=12-22$, preferably in the range $Z=15-20$, are radiation absorbing organic molecules and/or radiation absorbing salts. Preferably, the radiation absorbing organic molecules and/or radiation absorbing salts are water-soluble, non-volatile radiation absorbing organic compounds having a boiling point$\geq 200°$ C., and/or water-soluble, non-volatile radiation absorbing salts having a boiling point$\geq 200°$ C. Accordingly, in various embodiments, the ink compositions disclosed herein comprise radiation absorbing organic molecules composed of chemical elements having (a) a low-atomic number $1 \leq Z \leq 11$, preferably a low-atomic number $1 \leq Z \leq 8$; and/or (b) an atomic number in the range $Z=12-22$, preferably in the range $Z=15-20$, wherein the radiation absorbing organic molecules and/or radiation absorbing salts are water-soluble, non-volatile radiation absorbing organic compounds having a boiling point$\geq 200°$ C., and/or water-soluble, non-volatile radiation absorbing salts having a boiling point$\geq 200°$ C.

In various embodiments, reference to "radiation absorbing (organic) molecule(s)" may be considered as reference to "radiation absorbing (organic) compound(s)". Thus, where appropriate or necessary, the term "radiation absorbing (organic) molecule(s)" may be replaced by the term "radiation absorbing (organic) compound(s)".

In various embodiments, the radiation absorbing molecules composed of chemical elements having (a) a low-atomic number $1 \leq Z \leq 11$, preferably a low-atomic number $1 \leq Z \leq 8$; and/or (b) an atomic number in the range $Z=12-22$, preferably in the range $Z=15-20$, are radiation absorbing organic molecules (compounds) and/or radiation absorbing salts selected from any of: (i) sugars and derivatives thereof, preferably aldoses including glucose and mannose, ketoses including fructose, disaccharides including lactose, maltose and saccharose, sugar alcohols including sorbitole, and/or amino sugars including meglumin; (ii) pyridine-, pyrimidine-, purine-, imidazole-, pyrazole-, and/or indole derivatives; (iii) amino acids and derivatives thereof, preferably proline and lysine; (iv) carboxylic acids and derivatives thereof, preferably citric acid, tartaric acid, and/or amides including urea and caprolactam; (v) polymers having a low molecular weight$\leq 30$ kDa; and/or (vi) ammonium-lithium-, sodium- and/or magnesium-salts. Preferably, the radiation absorbing organic molecules (compounds) and/or radiation absorbing salts according to any of (i) to (vi) are water-soluble, non-volatile radiation absorbing compounds having a boiling point$\geq 200°$ C.

In various embodiments, the radiation absorbing molecules composed of chemical elements having (a) a low-atomic number $1 \leq Z \leq 11$, preferably a low-atomic number $1 \leq Z \leq 8$; and/or (b) an atomic number in the range $Z=12-22$, preferably in the range $Z=15-20$, are radiation absorbing salts selected from any of: (i) sodium, magnesium, aluminum salts; (ii) potassium salts, preferably potassium-chloride, -phosphate, -sulfate, -thiosulfate, -thiocyanate, and/or -diphosphate; (iii) calcium salts, preferably calcium chloride and nitrate; (iv) scandium salts; (v) titanium-salts; (vi) phosphates including di-, tri-, and poly-phosphates, hydrogenphosphates, dihydrogenphosphates, mono-, di-, tri-, and tetra-thiophosphates; phosphonates, phosphinates, (vii) sulfates including hydrogensulfates and thiosulfates; sulfites including hydrogensulfites, sulfides including hydrogensulfides, thiocyanates, isothiocyanates, di- and polythionates, (xiii) chlorides; (ix) chlorates; (x) perchlorates; and/or (xi) silicates. Preferably, the radiation absorbing salts according to any of (i) to (xi) are water-soluble, non-volatile compounds having a boiling point$\geq 200°$ C.

The ink compositions provided by the present disclosure are liquid, in particular liquid at room temperature. The viscosity of the liquid ink compositions may vary. In general, the viscosity of the ink compositions provided by the present disclosure is such that the ink compositions are printable on layers so as to generate a phantom/an imaging phantom as disclosed herein. In various embodiments, an ink composition provided by the present disclosure has a viscosity in the range of 1-30 mPa·s, preferably in the range between 2-15 mPa s. In various other embodiments, an ink composition provided by the present disclosure may have a viscosity in the range of 10-30 mPa·s, preferably in the range of 15-25 mPa·s, more preferably in the range of 17-22 mPa s. In various preferred embodiments, an ink composition provided by the present disclosure may have a viscosity$\leq 25$ mPa s, preferably $\leq 20$ mPa s, more preferably a viscosity$\leq 15$ mPa·s. In various other preferred embodiments, an ink composition provided by the present disclosure may have a viscosity$\leq 25$ mPa·s and $>5$ mPa·s, preferably a viscosity$\leq 20$ mPa·s and $>5$ mPa·s. In various further embodiments, an ink composition provided by the present disclosure may have a viscosity$\leq 15$ mPa s and $>5$ mPa·s, or a viscosity$\leq 10$ mPa·s and $>5$ mPa·s.

Preferably, the ink compositions are printable on layers at room temperature for generating a phantom/an imaging phantom as disclosed herein. Thus, the viscosity values disclosed herein preferably refer to the viscosity of the novel ink compositions provided herein at room temperature. The term "room temperature" is further described elsewhere herein. As further described herein, the term viscosity may refer to the shear viscosity, which expresses the resistance of a fluid to shearing forces, preferably the resistance of a fluid to shearing forces at room temperature. The viscosity may be determined/measured using a rheometer.

Accordingly, disclosed herein is an ink composition conferring radiation absorbing properties mimicking biological tissue, wherein the composition comprises dissolved radiation absorbing molecules composed of chemical elements having a low-atomic number $1 \leq Z \leq 11$, preferably a low-atomic number $1 \leq Z \leq 8$; and wherein the composition has a viscosity in the range between 1-30 mPa·s, preferably in the range between 2-15 mPa s. Also disclosed herein is an ink composition conferring radiation absorbing properties mimicking biological tissue, wherein the composition comprises dissolved radiation absorbing molecules composed of chemical elements having a low-atomic number $1 \leq Z \leq 11$, preferably a low-atomic number $1 \leq Z \leq 8$; and wherein the composition has a viscosity in the range of 10-30 mPa s, preferably in the range of 15-25 mPa s, more preferably in the range of 17-22 mPa s. In various preferred embodiments, the ink composition may have a viscosity $\leq 25$ mPa·s, preferably $\leq 20$ mPa·s, more preferably a viscosity $\leq 15$ mPa·s. The radiation absorbing molecules may be radiation absorbing organic molecules and/or salts, preferably water-soluble, non-volatile radiation absorbing organic molecules/compounds having a boiling point $\geq 200°$ C., and/or water-soluble, non-volatile radiation absorbing salts having a boiling point $\geq 200°$ C. More specifically, the radiation absorbing organic molecules or compounds and/or salts may be selected from any of: (i) sugars and derivatives thereof, preferably aldoses including glucose and mannose, ketoses including fructose, disaccharides including lactose, maltose and saccharose, sugar alcohols including sorbitole, and/or amino sugars including meglumin; (ii) pyridine-, pyrimidine-, purine-, imidazole-, pyrazole-, and/or indole derivatives; (iii) amino acids and derivatives thereof, preferably proline and lysine; (iv) carboxylic acids and derivatives thereof, preferably citric acid, tartaric acid, and/or amides including urea and caprolactam; (v) polymers having a low molecular weight $\leq 30$ kDa; and/or (vi) ammonium-lithium-, sodium- and/or magnesium-salts. Also, the radiation absorbing salts may be selected from any of: (i) sodium, magnesium, aluminum salts; (ii) potassium salts, preferably potassium-chloride, -phosphate, -sulfate, -thiosulfate, -thiocyanate, and/or -diphosphate; (iii) calcium salts, preferably calcium chloride and nitrate; (iv) scandium salts; (v) titanium-salts; (vi) phosphates including di-, tri-, and polyphosphates, hydrogenphosphates, dihydrogenphosphates, mono-, di-, tri-, and tetra-thiophosphates; phosphonates, phosphinates, (vii) sulfates including hydrogensulfates and thiosulfates; sulfites including hydrogensulfites, sulfides including hydrogensulfides, thiocyanates, isothiocyanates, di- and polythionates, (xiii) chlorides; (ix) chlorates; (x) perchlorates, and/or (xi) silicates.

In various embodiments, the ink composition conferring radiation absorbing properties mimicking biological soft tissue may comprise radiation absorbing molecules/compounds of any of the following:

Polyols Und Derivates Thereof, in Particular;

Saccharides (sugars) including mono-, di-, oligo-, poly-saccharides, preferably monosaccharides, more preferably pentoses and hexoses, in particular:

Aldoses: glyceraldehyde, erythrose, threose, ribose, arabinose, xylose, lyxose, allose, altrose, glucose, mannose, gulose, idose, galactose, talose.

Ketoses: dihydroxyacetone, erythrulose, ribulose, xylulose, psicose, fructose, sorbose, tagatose.

Disaccharides: cellobiose, gentiobiose, isomaltose, isomaltulose, lactose, lactulose, laminaribiose, maltose, maltulose, melibiose, neohesperidose, neotrehalose, nigerose, rutinose, sambubiose, sophorose, saccharose, trehalose.

Oligosaccharides: Raffinose, Maltotriose.

Aldoses are preferred radiation absorbing molecules/compounds, and particularly preferred aldoses are glucose and mannose.

In various embodiments, ketoses are preferred radiation absorbing molecules/compounds, and a particularly preferred ketose is fructose.

In various other embodiments, disaccharides are preferred radiation absorbing molecules/compounds, and particularly preferred disaccharides are lactose, maltose, and saccharose.

Sugar derivatives including amino sugars, acetylated amino sugars, alditols (sugar alcohols), in particular:

Alditoles: glycerol, erythritol, threitol, arabitol, xylitol, ribitol, mannitol, sorbitol, galactitol, fucitol, iditol, inositol, volemitol, isomalt, maltitol, lactitol. Sorbitol is a preferred alditole.

Amino sugars: meglumin, glucosamine, N-acetyl glucosamine, mannosamine, galactosamine, fructosamine. Meglumin is a preferred amino sugar, Polyvalent alcohols and derivatives thereof, in particular:

Phenol derivates: phenol, benzocatechin, resorcin, hydroquinone, pyrogallol,

Further Alcohols: pentaerythrite, tris(hydroxymethyl)aminomethane.

Pyridin-, pyrimidine-, purine-, imidazole-, pyrazole-, indole-derivatives, preferably those having a water solubility of >100 g/L.

Amino Acids/Peptides and Derivatives Thereof;

Amino acids, di- and oligopeptides, in particular:

Amino acids: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine.

Amino acids are preferred radiation absorbing molecules/compounds, and particularly preferred amino acids are Lysine and proline.

Betaines: N,N,N-Trimethylglycin.

Carboxylic Acids and Derivatives Thereof, Including Carboxylic Acids and Carboxylic Acid Esters, -Amides, -Imides, Lactone, and Lactame. In Particular;

Carboxylic acids: citric acid, tartaric acid, malic acid, isocitric acid, oxalic acid, gluconic acid, maleic acid, ketoglutaric acid, oxalo acetic acid, glutaric acid, ascorbic acid. Preferred carboxylic acids are citric acid and tartaric acid.

Amides: urea, N-methyl carbamide, N,N-dimethyl methyl carbamide, acetamide, caprolactam, valerolactam. Preferred amides are urea, N-methyl carbamide, N,N-dimethyl methyle carbamide, and caprolactam.

Esters: gluconolactone.

Water-Soluble Polymers and Derivatives Thereof, Including Those Having a Molecular Weight of $\leq 30$ kDa. In Particular:

Polyethylene glycole, polyethers, polyesters, polycarboxylic acids, polycaprolactames, polyvinylalcohol, polysaccharides, polyacrylic acids, polyvinylpyrrolidone, polycarboxylate, polyurethane, polyamines.

Preferred water-soluble polymers and derivatives thereof are those having a molecular weight of $\leq 30$ kDa.

Salts, in Particular:

cations: ammonium, lithium, (sodium).

anions: carbonate, nitrate, nitrite, fluoride, cyanide, carboxylates of mono-, di-, oligo- and polycarboxylic acids, in particular formate, acetate, propionate, oxalate, citrate, lactate. Preferred are ammonium formate, ammonium acetate, ammonium propionate, ammonium nitrate, lithium formate, lithium acetate, lithium propionate, lithium nitrate, lithium nitrite, and lithium lactate.

In various embodiments, the ink composition conferring radiation absorbing properties mimicking biological bone tissue may comprise radiation absorbing molecules/compounds/salts of any of the following:

cations: aluminum, potassium, calcium, scandium, titan. Preferred cations are potassium and calcium.

anions: phosphate, dihydrogenphosphate, hydrogenphosphate, di-, tri- and polyphosphate (+ any hydrogenphosphates), mono-, di-, tri- and tetrathiophosphate (+ any hydrogenthiophosphates), sulfate, hydrogensulfate, sulfite, hydrogensulfite, sulfide, hydrogensulfide, thiosulfate, chloride, chlorate, perchlorate. Preferred anions are phosphate, dihydrogenphosphate, hydrogenphosphate, diphosphate, sulfate, hydrogensulfate, thiosulfate, and chloride.

In various embodiments, the radiation absorbing salts may be any of:

Calcium salts: calcium acetate, calcium hydrogencarbonate, calcium chlorate, calcium chloride, calcium formate, calcium nitrate, calcium nitrite, calcium perchlorate, calcium propionate, calcium lactate, calcium gluconate. A preferred calcium salt is calcium chloride.

Potassium salts: potassium acetate, potassium carbonate, potassium chlorate, potassium chloride, potassium cyanide, potassium phosphate, potassium fluoride, potassium formate, potassium hydrogencarbonate, potassium nitrate, potassium nitrite, potassium oxalate, potassium perchlorate, potassium sulfate, potassium sulfide, potassium sulfite, potassium thiosulfate, potassium thiocyanate, potassium diphosphate, potassium polyphosphate, potassium metaphosphate, (+ any hydrogenphosphates, hydrogenthiophosphates, and hydrogencarbonates).

Potassium salts are preferred radiation absorbing molecules/compounds/salts, and particularly preferred are potassium chloride, potassium phosphate, potassium sulfate, potassium thiosulfate, potassium thiocyanate, and potassium diphosphate.

Sulfur compounds: lithium sulfate, sodium sulfate, ammonium sulfate, magnesium sulfate, lithium sulfite, sodium sulfite, potassium sulfite, ammonium sulfite, magnesium sulfite, lithium sulfide, sodium sulfide, ammonium sulfide, magnesium sulfide, lithium thiosulfate, sodium thiosulfate, potassium thiosulfate, ammonium thiosulfate, magnesium thiosulfate (+ any hydrogensulfates, -sulfites, and -sulfides).

Phosphorous compounds: lithium phosphate, sodium phosphate, ammonium phosphate, magnesium phosphate (+ any hydrogenphosphates, mono-, di-, tri-, and tetrathiophosphates as well as hydrogenthiophosphates).

Chloric compounds: lithium chloride, sodium chloride, potassium chloride, ammonium chloride, magnesium chloride, lithium chlorate, sodium chlorate, potassium chlorate, ammonium chlorate, magnesium chlorate, lithium perchlorate, sodium perchlorate, potassium perchlorate, ammonium perchlorate, and magnesium perchlorate.

In preferred embodiments of the ink compositions disclosed herein, the radiation absorbing organic compounds include sugars, more preferably saccharose. Thus, particularly preferred are water-soluble, non-volatile sugars having a boiling point≥200° C.

In other preferred embodiments of the ink compositions disclosed herein, the radiation absorbing organic compounds include amino acids, more preferably non-polar amino acids, even more preferably proline, and particularly preferred L-proline. Thus, particularly preferred are water-soluble, non-volatile amino acids having a boiling point≥200° C.

In preferred embodiments of the ink compositions disclosed herein, the radiation absorbing organic compounds preferably include sodium chloride. In particularly preferred embodiments, the ink composition comprises one or more non-volatile sugars having a boiling point≥200° C. and sodium chloride. Preferably, the sugar is saccharose. In other particularly preferred embodiments, the ink composition comprises one or more non-volatile sugars having a boiling point≥200° C., sodium chloride, and urea. Preferably, the sugar is saccharose.

In other particularly preferred embodiments, the ink composition comprises one or more non-volatile sugars having a boiling point≥200° C., and an amino acid. Preferably, the sugar is saccharose, and/or the amino acid is a non-polar amino acid, more preferably proline, even more preferably L-proline.

In other particularly preferred embodiments, the ink composition comprises one or more non-volatile sugars having a boiling point≥200° C., sodium chloride, and an amino acid. Preferably, the sugar is saccharose, and/or the amino acid is a non-polar amino acid, more preferably proline, even more preferably L-proline.

In further particularly preferred embodiments, the ink composition comprises one or more non-volatile sugars having a boiling point≥200° C., sodium chloride, urea, and an amino acid. Preferably, the sugar is saccharose, and/or the amino acid is proline, more preferably L-proline.

In still further particularly preferred embodiments, the ink composition comprises one or more non-volatile sugars having a boiling point≥200° C., sodium chloride, urea, an amino acid, and 2-pyrrolidon and/or a wetting agent. Preferably, the sugar is saccharose, and/or the amino acid is a non-polar amino acid, more preferably proline, even more preferably L-proline. The wetting agent preferably is IGEPAL-Co-630. The ink composition may further comprise a defoaming agent. In various embodiments, the defoaming agent is tributyl phosphate.

In other particularly preferred embodiments, the ink composition comprises one or more non-volatile sugars having a boiling point≥200° C., sodium chloride, urea, an amino acid, and 2-pyrrolidon and/or a defoaming agent. Preferably, the sugar is saccharose, and/or the amino acid is a non-polar amino acid, more preferably proline, even more preferably L-proline. In various embodiments, the defoaming agent is tributyl phosphate. The ink composition may further comprise a wetting agent. In various embodiments, the wetting agent is IGEPAL-Co-630. In particularly preferred embodiments, the wetting agent is IGEPAL-Co-630, and the defoaming agent is tributyl phosphate.

In other particularly preferred embodiments, the ink composition comprises one or more non-volatile sugars having a boiling point≥200° C., sodium chloride, urea, an amino acid, 2-pyrrolidon, a defoaming agent, and benzisothiazolinone. Preferably, the sugar is saccharose, and/or the amino acid is a non-polar amino acid, more preferably proline, even more preferably L-proline. In various embodiments, the defoaming agent is tributyl phosphate. The ink composition may further comprise a wetting agent. In various embodiments, the wetting agent is IGEPAL-Co-630. In particularly preferred embodiments, the wetting agent is IGEPAL-Co-630, and the defoaming agent is tri butyl phosphate.

In other particularly preferred embodiments, the ink composition comprises one or more non-volatile sugars having a boiling point≥200° C., sodium chloride, urea, an amino acid, 2-pyrrolidon, a defoaming agent, and benzisothiazolinone and/or malachite green oxalate. Preferably, the sugar is saccharose, and/or the amino acid is a non-polar amino acid, more preferably proline, even more preferably L-proline. In various embodiments, the defoaming agent is tributyl phosphate. The ink composition may further comprise a wetting agent. In various embodiments, the wetting agent is IGEPAL-Co-630. In particularly preferred embodiments, the wetting agent is IGEPAL-Co-630, and the defoaming agent is tributyl phosphate.

In various embodiments, the ink composition comprises any of: one or more non-volatile sugars having a boiling point≥200° C., sodium chloride, urea, an amino acid, a wetting agent, a defoaming agent, benzisothiazolinone, malachite green oxalate, and/or 2-pyrrolidon. Preferably, the sugar is saccharose, and/or the amino acid is a non-polar amino acid, more preferably proline, even more preferably L-proline. In various embodiments, the wetting agent is IGEPAL-Co-630. In various embodiments, the defoaming agent is tributyl phosphate. In preferred embodiments, the wetting agent is IGEPAL-Co-630, and the defoaming agent is tributyl phosphate.

In other particularly preferred embodiments, the ink composition comprises one or more non-volatile sugars having a boiling point≥200° C., potassium chloride, and an amino acid. Preferably, the sugar is saccharose, and/or the amino acid is a non-polar amino acid, more preferably proline, even more preferably L-proline.

In further particularly preferred embodiments, the ink composition comprises one or more non-volatile sugars having a boiling point≥200° C., potassium chloride, an amino acid, and 2-pyrrolidone. Preferably, the sugar is saccharose, and/or the amino acid is proline, more preferably L-proline.

In still further particularly preferred embodiments, the ink composition comprises one or more non-volatile sugars having a boiling point≥200° C., potassium chloride, an amino acid, and 2-pyrrolidon and/or an acidic compound. Preferably, the sugar is saccharose, and/or the amino acid is a non-polar amino acid, more preferably proline, even more preferably L-proline. The acidic compound preferably is Eosin B.

In various embodiments, the ink composition comprises any of: one or more non-volatile sugars having a boiling point≥200° C., potassium chloride, an amino acid, and 2-pyrrolidon and/or an acidic acid. Preferably, the sugar is saccharose, and/or the amino acid is a non-polar amino acid, more preferably proline, even more preferably L-proline.

In various embodiments, the radiation absorbing molecules and/or radiation absorbing salts composed of elements having a low-atomic number $1 \leq Z \leq 11$, preferably a low-atomic number $1 \leq Z \leq 8$, are present in the ink compositions disclosed herein in an amount of at least 75% w/w, preferably at least 80% w/w, relative to the total dry weight of the dissolved radiation absorbing molecules and/or radiation absorbing salts. The corresponding ink compositions confer radiation absorbing properties mimicking in particular biological soft tissue. Preferably, the remaining amount of 25% w/w or less, or 20% w/w or less, respectively, relative to the total dry weight of the dissolved radiation absorbing molecules and/or radiation absorbing salts comprise radiation absorbing molecules and/or radiation absorbing salts composed of elements having an atomic number in the range $Z=12-22$, preferably in the range $Z=15-20$. More preferably, the amount of radiation absorbing molecules and/or radiation absorbing salts composed of elements having an atomic number>22 present in the composition does not exceed 2% w/w, preferably does not exceed 1% w/w, relative to the total dry weight of the dissolved radiation absorbing molecules and/or radiation absorbing salts.

In various embodiments, the radiation absorbing molecules and/or radiation absorbing salts composed of elements having a low-atomic number $1 \leq Z \leq 11$, preferably a low-atomic number $1 \leq Z \leq 8$, are present in the ink compositions disclosed herein in an amount of at least 85% w/w, preferably at least 90% w/w, more preferably at least 95% w/w, relative to the total dry weight of the dissolved radiation absorbing molecules and/or radiation absorbing salts. Preferably, the remaining amount of 15% w/w or less, or 10% w/w or less, or 5% w/w or less, respectively, relative to the total dry weight of the dissolved radiation absorbing molecules and/or radiation absorbing salts comprise radiation absorbing molecules and/or radiation absorbing salts composed of elements having an atomic number in the range $Z=12-22$, preferably in the range $Z=15-20$. More preferably, the amount of radiation absorbing molecules and/or radiation absorbing salts composed of elements having an atomic number>22 present in the composition does not exceed 2% w/w, preferably does not exceed 2% w/w, relative to the total dry weight of the dissolved radiation absorbing molecules and/or radiation absorbing salts.

In various embodiments, the radiation absorbing molecules and/or radiation absorbing salts composed of elements having an atomic number in the range $Z=12-22$, preferably in the range $Z=15-20$, are present in the ink compositions disclosed herein in an amount of at least 50% w/w, preferably at least 70% w/w, relative to the total dry weight of the dissolved radiation absorbing molecules and/or radiation absorbing salts. The corresponding ink compositions confer radiation absorbing properties mimicking in particular biological bone tissue. Preferably, the remaining amount of 50% w/w or less, or 30% w/w or less, respectively, relative to the total dry weight of the dissolved radiation absorbing molecules and/or radiation absorbing salts comprise radiation absorbing molecules and/or radiation absorbing salts composed of elements having a low-atomic number $1 \leq Z \leq 11$, preferably a low-atomic number $1 \leq Z \leq 8$. More preferably, the amount of radiation absorbing molecules and/or radiation absorbing salts composed of elements having an atomic number in the range $Z>22$ present in the ink composition does not exceed 5% w/w, preferably does not exceed 4% w/w, more preferably does not exceed 3% w/w, relative to the total dry weight of the dissolved radiation absorbing molecules and/or radiation absorbing salts.

In various embodiments, the radiation absorbing molecules and/or radiation absorbing salts composed of elements having an atomic number in the range $Z=12-22$, preferably in the range $Z=15-20$, are present in the ink compositions disclosed herein in an amount of at least 60% w/w, preferably at least 80% w/w, relative to the total dry weight of the dissolved radiation absorbing molecules and/ or radiation absorbing salts. Preferably, the remaining amount of 40% w/w or less, or 20% w/w or less, respectively, relative to the total dry weight of the dissolved radiation absorbing molecules and/or radiation absorbing salts comprise radiation absorbing molecules and/or radiation absorbing salts composed of elements having a low-atomic number $1 \leq Z \leq 11$, preferably a low-atomic number $1 \leq Z \leq 8$. More preferably, the amount of radiation absorbing molecules and/or radiation absorbing salts composed of elements having an atomic number in the range $Z>22$ present in the composition does not exceed 5% w/w, preferably does not exceed 4% w/w, more preferably does not exceed 3% w/w, relative to the total dry weight of the dissolved radiation absorbing molecules and/or radiation absorbing salts.

In various embodiments, radiation preferably means ionizing radiation. Accordingly, radiation absorbing molecules and/or radiation absorbing salts as described herein preferably are ionizing radiation absorbing molecules and/or ionizing radiation absorbing salts. Gamma rays, X-rays, and the higher ultraviolet part of the electromagnetic spectrum are ionizing, whereas the lower ultraviolet part of the electromagnetic spectrum, and also the lower part of the spectrum below UV, including visible light, infrared, microwaves, and radio waves may all be considered non-ionizing radiation. In various embodiments of the present disclosure, ionizing radiation preferably encompasses photon energies in the range of 20 keV to 100 MeV. In various embodiments, ionizing radiation may be considered to encompass photon energies in the range of 20 keV to 50 MeV. In the present disclosure, ionizing radiation preferably includes gamma rays and X-rays (which are electromagnetic, indirectly ionizing radiation). Some examples of X-rays used in medicine are: superficial X-rays—35 to 60 keV; diagnostic X-rays—20 to 150 keV; orthovoltage X-rays—200 to 500 keV; supervoltage X-rays—500 to 1,000 keV; megavoltage X-rays—1 to 25 MeV. These examples of X-rays are incorporated as embodiments into the present disclosure. Megavoltage X-rays are by far most common in radiotherapy for treatment of a wide range of cancers.

It has surprisingly been found that the novel ink compositions provided by the present disclosure allow the realistic simulation of the radiation absorption properties of biological tissue over the energy range relevant for computed tomography (CT) and radiotherapy (RT). The photon energy range in CT and RT is shown in FIG. 1. The ink compositions provided by the present disclosure can confer radiation absorbing properties mimicking the radiation absorbing properties of biological tissue at a photon energy or photon energies (including one or more photon energies) in the range of 20 keV to 50 MeV. Accordingly, the (imaging) phantoms disclosed herein built up of layers carrying the radiation absorbing molecules and/or radiation absorbing salts of the ink compositions provided by the present disclosure exhibit radiation absorbing properties mimicking biological tissue at photon energies in the range of 20 keV to 50 MeV.

Furthermore, the ink compositions provided by the present disclosure advantageously allow achieving a high material disposition in a phantom/an imaging phantom as disclosed herein. This is provided for, inter alia, by the high concentration of dissolved radiation absorbing molecules and/or radiation absorbing salts present in the ink compositions. Actually, it has surprisingly been found that a phantom/an imaging phantom generated using a novel ink composition provided by the present disclosure shows densities and attenuation coefficients similar to human tissue.

The ink compositions disclosed herein can confer to a phantom/an imaging phantom, which is generated with the ink compositions disclosed herein, a mass attenuation coefficient $\mu/\rho$ value≤0.2 cm$^2$/g at, e.g., 100 keV, preferably in the range of 0.160-0.195 cm$^2$/g at, e.g., 100 keV. Specifically, the radiation absorbing molecules and/or radiation absorbing salts of the ink compositions disclosed herein can confer to a phantom/an imaging phantom, which is generated with the ink compositions disclosed herein, a mass attenuation coefficient $\mu/\rho$ value≤0.2 cm$^2$/g at 100 keV, preferably in the range of 0.160-0.195 cm$^2$/g at, e.g., 100 keV. In various embodiments, the mass attenuation coefficient $\mu/\rho$ value is below 0.170 cm$^2$/g at, e.g., 100 keV. Accordingly, disclosed herein are (imaging) phantoms that exhibit such mass attenuation coefficient values conferred by novel ink compositions or by the radiation absorbing molecules and/or radiation absorbing salts of the novel ink compositions, respectively.

In various embodiments pertaining to a phantom/an imaging phantom mimicking the radiation properties of biological soft tissue, the attenuation coefficient $\mu/\rho$ value preferably is in the range of 0.160-0.195 cm$^2$/g at, e.g., 100 keV, more preferably in the range of 0.160-0.175 cm$^2$/g at, e.g., 100 keV, even more preferably in the range of 0.165-0.172 cm$^2$/g at, e.g., 100 keV.

In various other embodiments pertaining to a phantom/an imaging phantom mimicking the radiation properties of biological bone tissue, the attenuation coefficient $\mu/\rho$ value preferably is in the range of 0.165-0.200 cm$^2$/g at, e.g., 100 keV, more preferably in the range of 0.172-0.195 cm$^2$/g at, e.g., 100 keV.

In various other embodiments pertaining to a phantom/an imaging phantom mimicking the radiation properties of both biological bone and soft tissue, the attenuation coefficient $\mu/\rho$ value preferably is in the range of 0.165-0.195 cm$^2$/g at, e.g., 100 keV.

As described herein, the mass attenuation coefficient values preferably represent X-ray mass attenuation coefficient values.

It has been surprisingly found that the mass attenuation coefficient of a phantom/an imaging phantom, which is generated with the ink compositions disclosed herein, shows only little deviation, i.e., is substantially similar, to the mass attenuation coefficient of a corresponding target biological tissue. Specifically, the radiation absorbing molecules and/or radiation absorbing salts of the ink compositions disclosed herein can provide for a maximum deviation of the mass attenuation coefficient of less than about 5%, preferably less than about 4%, with respect to the mass attenuation coefficient of a corresponding target biological tissue, at photon energies in the range of 20 keV to 100 MeV. This may be considered to be within the estimation error of the values for biological tissues.

Accordingly, (imaging) phantoms are provided, which are generated with the ink compositions disclosed herein, and which show a maximum deviation of the mass attenuation coefficient of less than about 5%, preferably less than about 4%, with respect to the mass attenuation coefficient of a corresponding target biological tissue, at photon energies in the range of 20 keV to 100 MeV.

Thus, a phantom/an imaging phantom exhibiting radiation absorbing properties mimicking biological tissue at photon energies in the range of 20 keV to 100 MeV as disclosed herein preferably is a phantom/an imaging phantom showing a mass attenuation coefficient at photon energies in the range of 20 keV to 100 MeV, wherein the mass attenuation coefficient is within 5% (deviation), preferably within 4% (deviation), of the values for the corresponding target biological tissue, which may be considered to be within the estimation error of these values.

In preferred embodiments, a phantom/an imaging phantom exhibiting radiation absorbing properties mimicking biological tissue at photon energies in the range of 20 keV to 100 MeV as disclosed herein shows a mass attenuation coefficient at photon energies in the range of 20 keV to 100 MeV, wherein the mass attenuation coefficient is within 3.5% (deviation) of the values for the corresponding target biological tissue. Preferably the corresponding target biological tissue is muscle tissue, more preferably skeletal muscle tissue. More preferably, the muscle tissue or skeletal muscle tissue is mammalian muscle tissue or mammalian skeletal muscle tissue, respectively. Still more preferably, the mammalian muscle tissue or mammalian skeletal muscle tissue is human muscle tissue or human skeletal muscle tissue, respectively.

In preferred embodiments, a phantom/an imaging phantom exhibiting radiation absorbing properties mimicking biological tissue at a photon energy or photon energies (including one or more photon energies) in the range of 20 keV to 100 MeV as disclosed herein shows a mass attenuation coefficient at a photon energy or photon energies (including one or more photon energies) in the range of 20 keV to 100 MeV, wherein the mass attenuation coefficient is within 1.0% (deviation) of the values for the corresponding target biological tissue. Preferably the corresponding target biological tissue is bone tissue, more preferably cortical bone tissue. More preferably, the bone tissue or cortical bone tissue is mammalian bone tissue or mammalian cortical bone tissue, respectively. Still more preferably, the mammalian bone tissue or mammalian cortical bone tissue is human bone tissue or human cortical bone tissue, respectively.

The mass attenuation coefficient of a corresponding target biological tissue may be measured or calculated based on the values for the chemical/elemental composition of the respective biological tissue, which values are available from the literature. Specifically, mass attenuation coefficients of phantom materials, including imaging phantoms provided by the present disclosure, may be estimated based on reference to, e.g., elemental compositions from the USDA National Nutrient Database for Standard Reference and biological (human) values from the literature.

The (imaging) phantom preferably has a size similar to a subject or the corresponding biological tissue, respectively. Correlations between subject data and phantom data can be considered to be within the error bars of measurement. As disclosed herein, the subject preferably is a mammalian subject, including a human or animal subject. More preferably, the mammalian subject is a human subject. In various embodiments of the present disclosure, the terms "subject" and "patient" may be used interchangeably.

The radiation absorbing molecules and/or radiation absorbing salts are present in the ink compositions provided herein in dissolved form. Preferably, the radiation absorbing molecules and/or radiation absorbing salts are soluble in the ink compositions disclosed herein at room temperature. In various embodiments, the radiation absorbing molecules and/or radiation absorbing salts are soluble at a temperature of 25° C. Preferably, the radiation absorbing molecules and/or radiation absorbing salts are soluble in water at room temperature. In various embodiments, the radiation absorbing molecules and/or radiation absorbing salts are soluble in water at a temperature of 25° C.

In various embodiments, the ink compositions provided by the present disclosure are based on a hydrophilic solvent, preferably an aqueous solvent. The aqueous solvent may contain one or more (hydrophilic) organic solvents. In various embodiments, the solvent may be any of water, alcohol, or a mixture of hydrophilic solvents including water. For example, the solvent may be a mixture of water and alcohol. In preferred embodiments, the alcohol is 2-propanol.

In various other embodiments, the ink compositions provided by the present disclosure are water-based and essentially or substantially free of organic solvents.

In various embodiments, the ink compositions provided by the present disclosure may be essentially or substantially free of any dyes, including synthetic and/or organic dyes.

As described herein, the term "room temperature" may comprise a range of 15-30° C., preferably a range of 18-28° C., more preferably a range of 20-25° C., even more preferably a range of 22-25° C. In various embodiments, the term "room temperature" means a temperature of 25° C.

In various embodiments, the ink compositions provided by the present disclosure have a surface tension in the range of 20-70 mN/m, preferably in the range between 30-50 mN/m. In various embodiments, the ink compositions provided by the present disclosure have a surface tension in the range of 20-70 mN/m, preferably in the range between 30-50 mN/m, and a viscosity in the range of 1-30 mPa·s, preferably in the range between 2-15 mPa s. In various other embodiments, an ink composition provided by the present disclosure have a surface tension in the range of 20-70 mN/m, preferably in the range between 30-50 mN/m, and have a viscosity in the range of 10-30 mPa·s, preferably in the range of 15-25 mPa·s, more preferably in the range of 17-22 mPa s. In various preferred embodiments, an ink composition provided by the present disclosure has a surface tension in the range of 20-70 mN/m, preferably in the range between 30-50 mN/m, and has a viscosity≤25 mPa·s, preferably ≤20 mPa·s, more preferably a viscosity≤15 mPa·s. In various other preferred embodiments, an ink composition provided by the present disclosure has a surface tension in the range of 20-70 mN/m, preferably in the range between 30-50 mN/m, and has a viscosity≤25 mPa s and >5 mPa s, preferably a viscosity≤20 mPa s and >5 mPa·s. In various further embodiments, an ink composition provided by the present disclosure has a surface tension in the range of 20-70 mN/m, preferably in the range between 30-50 mN/m, and has a viscosity≤15 mPa·s and >5 mPa s, or a viscosity≤10 mPa s and >5 mPa·s.

The (imaging) phantoms provided by the present disclosure are (capable of) mimicking the radiation absorbing properties of biological soft tissue and/or biological bone tissue. In various embodiments, the (imaging) phantoms provided by the present disclosure have a Hounsfield Unit (HU) value between −200 and +300 in a CT scan with a tube voltage of 120 kV; and/or have a Hounsfield Unit (HU) value between −50 and +3.000 in a CT scan with a tube voltage of 120 kV.

In various embodiments, the (imaging) phantoms provided by the present disclosure are (capable of) mimicking the radiation absorbing properties of biological soft tissue and have a Hounsfield Unit (HU) value between −200 and +300 in a CT scan with a tube voltage of 120 kV.

In various other embodiments the (imaging) phantoms provided by the present disclosure are (capable of) mimicking the radiation absorbing properties of biological bone tissue, and have a Hounsfield Unit (HU) value between −50 and +3000 in a CT scan with a tube voltage of 120 kV.

In various embodiments, the (imaging) phantoms provided by the present disclosure are (capable of) mimicking the radiation absorbing properties of biological soft and bone tissue, and have a Hounsfield Unit (HU) value between −200 and +3000 in a CT scan with a tube voltage of 120 kV.

In various embodiments, the (imaging) phantoms provided by the present disclosure are (capable of) mimicking the radiation absorbing properties of biological cortical bone tissue; and/or has a Hounsfield Unit (HU) value between −50 and +3000 in a CT scan with a tube voltage of 120 kV.

Preferably, the (imaging) phantoms provided by the present disclosure have a Hounsfield Unit (HU) value between −100 and +200 in a CT scan with a tube voltage of 120 kV; and/or have a Hounsfield Unit (HU) value between +100 and +2.500 in a CT scan with a tube voltage of 120 kV. More preferably, the (imaging) phantoms provided by the present disclosure have a Hounsfield Unit (HU) value between −50 and +150 in a CT scan with a tube voltage of 120 kV; and/or have a Hounsfield Unit (HU) value between +301 and +2.000 in a CT scan with a tube voltage of 120 kV.

With increasing photon energy from 80-135 keV, a phantom/an imaging phantom (soft tissue) provided by the present disclosure may show constant to slightly increasing CT values in the range of approximately −100 to +100 Hounsfield Units (HU). Furthermore, a phantom/an imaging phantom (bone tissue) provided by the present disclosure may show higher CT values of up to +1400 Hounsfield Units (HU) that are decreasing with increasing photon energy from 80-135 keV.

In various embodiments of the (imaging) phantoms disclosed herein, which are built up of layers carrying the radiation absorbing molecules and/or radiation absorbing salts of the ink compositions provided by the present disclosure, the layers are multiple layers, which are preferably stacked. Accordingly, in various embodiments, the (imaging) phantoms disclosed herein are built up of stacks generated from multiple layers carrying the radiation absorbing molecules and/or radiation absorbing salts of the ink compositions provided by the present disclosure. In various embodiments, each stack comprises at least two layers and has a thickness of at least 80 μm. More preferably, each stack comprises at least 10 layers and has a thickness of at least 400 μm, even more preferably each stack comprises at least 50 layers and has a thickness of at least 2 mm.

The layers may have a thickness as low as about 1 μm. Accordingly, described herein are layers having a thickness of at least 1 μm. The layers may have a thickness in the range of about 1 μm to about 5.000 μm (5 mm), preferably in the range of about 10 μm to about 2.000 μm, more preferably in the range of about 20 μm to about 1.000 μm, even more preferably in the range of about 30 μm to about 500 μm. Particularly preferred are layers having a thickness in the range of about 30 μm to about 100 μm. In various embodiments, the layer has a thickness in the range of about 30 μm to about 50 μm. In various other embodiments, the layer has a thickness in the range of about 35 μm to about 45 μm, preferably the layer has a thickness of about 40 μm. In various embodiments, the layer has a thickness of at least 25 μm, preferably of at least 30 μm, more preferably of at least 35 μm, and even more preferably of at least 40 μm. In various other embodiments, the layer has a thickness in the range of about 60 μm to about 100 μm, preferably the layer has a thickness of about 80 μm.

In various embodiments, each stack comprises at least two layers and has a thickness of at least 80 μm, wherein each layer has a thickness of about or at least 40 μm. More preferably, each stack comprises at least 10 layers and has a thickness of at least 400 μm, wherein each layer has a thickness of about or at least 40 μm. Even more preferably, each stack comprises at least 50 layers and has a thickness of at least 2 mm (2.000 μm), wherein each layer has a thickness of about or at least 40 μm.

Accordingly, in various embodiments, the (imaging) phantoms disclosed herein are built up of stacks generated from multiple layers carrying the radiation absorbing molecules and/or radiation absorbing salts of the ink compositions provided by the present disclosure, wherein each layer has a thickness of at least 40 μm. Preferably, each layer comprises pulp material, preferably cellulose, and/or comprises a thermoplastic coating, preferably a polyethylene coating, on one side of its surface. In various embodiments of the (imaging) phantoms provided by the present disclosure, the weight ratio of layer material to thermoplastic coating is in the range of 1:1 to 20:1, preferably in the range of 5:1 to 10:1. Preferably, the thermoplastic coating is a thermoplastic polymer material having a melting point below 200° C. In various embodiments, the polymer material may be any of polyamide, polycaprolactone, polyethylene, polylactic acid, polyoxymethylene, polyurethane, polypropylene, polyvinyl chloride, and poly(ethylene-vinyl acetate).

In preferred embodiments, the (imaging) phantoms disclosed herein comprise stacks of multiple layers, wherein the multiple layers are glued layers.

In various embodiments of the (imaging) phantoms disclosed herein, the weight ratio of the ink composition-derived radiation absorbing molecules:layer material is between 0.01:2 to 1:2.

Disclosed herein is the use of the ink compositions provided by the present disclosure for generating a phantom/an imaging phantom. Starting, e.g., from a standard CT scan of a subject, the grey scale encoded CT data set is first processed into printable data. Radiopaque printing can be carried out using inkjet technology to print the processed CT images to a phantom base material using, e.g., a water-based radiopaque ink composition provided herein with printing resolution of, e.g., 600 dpi. As base material, paper with a certain chemical composition may be used. In particular, the paper may be coated on one side with a thin layer of a thermoplastic to allow temperature-controlled agglutination of the single papers. Thin stacks of paper may be glued together and cutted to outer and inner contours using, e.g., a laser cutter. In a further step, the stacks can be put together to build the complete phantom. A phantom manufacturing process, in which the novel ink compositions provided by the present disclosure can be applied to, is exemplified in FIG. 4.

A novel method of generating a phantom/an imaging phantom provided by the present disclosure is exemplified in FIG. 10. The novel method of generating a phantom/an imaging phantom exhibiting radiation absorbing properties mimicking human tissue provided by the present disclosure comprises a step of printing an ink composition as disclosed herein onto multiple layers (which layers make up the phantom base material). The method may include printing the ink composition using an ink jet printer. Preferably, the method may further comprise glue coating of the layers, more preferably glue coating followed by heat pressing and stacking of the layers. In various embodiments, the heat pressing may be carried out at a temperature in the range of 90° C. to 130° C., preferably in the range of 100° C. to 120° C., more preferably in the range of 105° C. to 115° C., even more preferably at a temperature of 110° C. The novel method advantageously comprises a heat gluing subsequent to the step of heat pressing and stacking of the layers. In various embodiments, the heat gluing may be carried out at a temperature in the range of 90° C. to 130° C., preferably in the range of 100° C. to 120° C., more preferably in the range of 105° C. to 115° C., even more preferably at a temperature of 110° C. Prior to the heat gluing, the heat-pressed and stacked layers may undergo a cutting step for tailoring or customization of the phantom, i.e., the contours of the phantom are cut and trimmed. Truncated paper is usually removed. This way, the method provides an individual phantom after the heat gluing. The step of heat gluing may preferably be performed in a heat incubator. Furthermore, the cutting step may preferably be performed with a laser cutter. Accordingly, the present disclosure provides a novel method of generating a phantom/an imaging phantom, preferably an anthropomorphic phantom, wherein the method comprises a step of printing an ink composition as disclosed herein onto multiple layers, preferably onto paper sheets, and a step of coating the paper sheets printed with the novel ink composition with glue. The method preferably includes the use of an inkjet printer in the step printing the ink composition onto multiple layers. The method further comprises a step of pressing and stacking, preferably heat pressing and stacking, the glue-coated layers to generate stacks of multiple layers, in accordance with the stacks of multiple layers described elsewhere herein. The method further comprises a step of cutting the pressed and stacked layers, wherein the cutting step preferably is performed with a laser cutter. This step provides for tailoring or customization of the individual phantom. The method preferably further comprises a step of heat gluing the cutted stacks of the individual phantom, wherein the step of heat gluing may preferably be performed in a heat incubator. As mentioned above, the novel method of generating a phantom/an imaging phantom provided by the present disclosure is exemplified in FIG. 10.

Biological tissue will be simulated by printing the novel radiopaque ink compositions provided herein on the phantom base material (i.e., the layer material). Accordingly, in the novel manufacturing processes disclosed herein, the phantom base material (i.e., the layer material) is suitable to simulate all types of biological tissue (in particular human and/or animal tissue) with a density greater than $0.9$ g/cm$^3$ (cf. Table 1), more preferably greater than $0.93$ g/cm$^3$. Preferably, the phantom base material (i.e., the layer material) is suitable to simulate all types of biological tissue (in particular human and/or animal tissue) with a density greater than $1.0$ g/cm$^3$ (cf. Table 1), more preferably greater than $1.04$ g/cm$^3$. In various embodiments, the phantom base material (i.e., the layer material) is suitable to simulate all types of biological tissue (in particular human and/or animal tissue) with a density in the range of $1.0$ g/cm$^3$ to $2.0$ g/cm$^3$, even more preferably in the range of $1.0$ g/cm$^3$ up to (and including) $1.92$ g/cm$^3$ (cf. Table 1).

The novel ink compositions provided by the present disclosure can confer this property of mimicking or simulating (all types of) biological tissue (in particular human and/or animal tissue) or organ (in particular human and/or animal organ(s)) with a density greater than $0.9$ g/cm$^3$ to the phantom layer material, and thus to a phantom/an imaging phantom as disclosed herein.

In various embodiments, the radiation absorption characteristics/properties of the novel (imaging) phantoms disclosed herein are resulting out of the combination of phantom base material (i.e., the layer material) and the radiation absorbing molecules or compounds dissolved in the novel radiopaque ink compositions provided herein that remain absorbed in the base (carrier) material after evaporation of the solvent, i.e., after evaporation of all volatile ink compounds. Accordingly, the radiation absorption properties of the phantom base material may be adjusted to the desired values (in particular to the density of biological tissue or biological organ), e.g., by adding specifically radiation absorbing materials. The phantom base material or layer material is preferably composed of chemical elements having a low-atomic number $1 \leq Z \leq 11$, preferably a low-atomic number $1 \leq Z \leq 8$. More preferably, the phantom base material or layer material is composed of chemical elements having a low-atomic number $1 \leq Z \leq 11$, preferably a low-atomic number $1 \leq Z \leq 8$, and is adjusted to a biological tissue (in particular human and/or animal tissue) density greater than $0.9$ g/cm$^3$. Even more preferably, the phantom base material or layer material is composed of chemical elements having a low-atomic number $1 \leq Z \leq 11$, preferably a low-atomic number $1 \leq Z \leq 8$, and is adjusted to a biological tissue (in particular human and/or animal tissue) density greater than $0.9$ g/cm$^3$ and a CT value of about $-120$ HU at a tube voltage of $120$ kV. In various embodiments, the phantom base material or layer material is adjusted to a biological tissue (in particular human and/or animal tissue) density greater than $0.93$ g/cm$^3$. Preferably, the phantom base material (i.e., the layer material) is adjusted to a biological tissue (in particular human and/or animal tissue) density greater than $1.0$ g/cm$^3$ (cf. Table 1), more preferably greater than $1.04$ g/cm$^3$. In various embodiments, the phantom base material (i.e., the layer material) is adjusted to a biological tissue (in particular human and/or animal tissue) density in the range of $1.0$ g/cm$^3$ to $2.0$ g/cm$^3$, even more preferably in the range of $1.0$ g/cm$^3$ up to (and including) $1.92$ g/cm$^3$ (cf. Table 1).

In various embodiments, a phantom/an imaging phantom as disclosed herein may comprise between about 50-60% phantom base material, and between about 40-50% radiation absorbing molecules or compounds or salts absorbed in the base (carrier) material, wherein the radiation absorbing molecules or compounds or salts are mimicking biological bone tissue, preferably biological cortical bone. Preferably, a phantom/an imaging phantom as disclosed herein may comprise between about 50-55% phantom base material, and between about 45-50% radiation absorbing molecules or compounds or salts absorbed in the base (carrier) material. In various embodiments, a phantom/an imaging phantom as disclosed herein may comprise phantom base material and radiation absorbing molecules or compounds absorbed in the base (carrier) material in a ratio of about 1.3:1, wherein the ink composition comprises radiation absorbing molecules or salts mimicking cortical bone.

In various embodiments of the present disclosure, the combination of (soft tissue) ink composition and phantom base material may cover a density range from $0.9$ to about $1.2$ g/cm$^3$, and may preferably cover a CT value range from $-120$ to $+150$ HU, preferably at a tube voltage of $120$ kV. For the simulation of human bone tissue, the combination of (bone tissue) ink composition and phantom base material may cover a density range from $0.9$ to about $1.95$ g/cm$^3$, and may preferably cover a CT value range from $-120$ to $+1400$ HU, preferably at a tube voltage of $120$ kV.

In various embodiments, the phantom base material is comprised of the carrier material (i.e., the layer material) and a coating, preferably a thermoplastic coating.

To allow radiopaque printing of CT images, the carrier material needs to be processable in thin sheets, preferably thin sheets with a thickness of approximately $0.05$-$0.2$ mm. The layers (or layer material or carrier material; the terms may be used interchangeably herein) may have a thickness as low as about 1 µm. Accordingly, described herein are layers having a thickness of at least 1 µm. The layers may have a thickness in the range of about 1 µm to about 5.000 µm, preferably in the range of about 10 µm to about 2.000 µm, more preferably in the range of about 20 µm to about 1.000 µm, even more preferably in the range of about 30 µm to about 100 µm. Particularly preferred are layers having a thickness in the range of about 40 µm to about 60 µm, preferably the layer has a thickness of about 50 µm. In various embodiments, the layer has a thickness in the range of about 35 µm to about 45 µm, preferably the layer has a thickness of about 40 µm. In various embodiments, the layer has a thickness of at least 35 µm, preferably of at least 40 µm, more preferably of at least 45 µm, and even more preferably of at least 50 µm.

The layer material used in the methods disclosed herein is capable of absorbing liquid ink compositions or liquid ink solutions, in particular liquid ink compositions or liquid ink solutions used to adjust the layer material to a biological tissue (in particular human and/or animal tissue) density of up to 1.92 g/cm$^3$ (cf. Table 1—maximum bone density in the human body). The novel methods of generating an imaging phantom provided by the present disclosure advantageously allow applying different layer materials, in particular different paper qualities, to be printed with the novel ink compositions.

Preferably, the layer material as disclosed herein does have no or only moderate hygroscopy.

Different types of biological tissue may be simulated by formulating different ink compositions and/or by combining different amounts of one or multiple ink compositions with the phantom base material. The ratio of ink composition to phantom base material may thereby be calculated from the density of the target biological tissue. To simulate all types of biological soft tissue, the combination of (soft tissue) ink composition and phantom base material may cover a density range from 0.9 to about 1.2 g/cm$^3$, and may preferably cover a CT value range from −120 to +150 HU, preferably at a tube voltage of 120 kV (see Table 2 in the Examples section). For the simulation of biological bone tissue, the combination of (bone tissue) ink composition and phantom base material may cover a density range from 0.9 to about 1.95 g/cm$^3$, and may preferably cover a CT value range from −120 to +1400 HU, preferably at a tube voltage of 120 kV (see Table 2 in the Examples section).

Cavities or tissue with densities below 0.9 g/cm$^3$ can be simulated in the novel (imaging) phantoms by making, e.g., cut outs, perforations, or by placing insets of foamed plastic into the phantom (see Table 2 in the Examples section).

For example, a phantom base material that meets the requirements may be a kraft paper with a grammage of 60 g/m$^2$, which is preferably coated on one side with a layer of low density polyethylene with a grammage of 8 g/m$^2$. The material may only consist of hydrogen, carbon and oxygen with a composition given in Table 3 (see Examples section). The polyethylene firmly sticks to the kraft paper. Stacking of the base material to three-dimensional objects is carried out by pressing the sheets together at a temperature of 110° C., whereby the polyethylene molds and firmly glues the sheets together. The applied pressure can be adjusted so that the final phantom material has a density of 0.9 g/cm$^3$.

The novel method provided herein is not limited with respect to the height of the stacks or the phantom, respectively. Furthermore, the novel method advantageously provides for a homogenous coating of glue onto the layers. Still further, the novel method of generating a phantom/an imaging phantom provided by the present disclosure is independent of existing 3D printing methods, although this does not exclude that the novel ink composition provided herein is applied in a method of generating a phantom/an imaging phantom using 3D printing technology, in particular paper-based 3D printing technology. In particular, disclosed herein are such methods using the selective deposition lamination (SDL) or laminated object manufacturing (LOM) technology, which are hybrid methods combining additive and subtractive manufacturing. In particular, after loading the 3D printer with paper (preferably A4 format), the ink is sprayed on the paper, while a binding agent provides for gluing the paper sheets together. Using a cutting knife, the contours of the object (phantom) are cut and trimmed. Truncated paper is usually removed.

In various embodiments, the method comprises generating stacks of multiple layers, preferably wherein each stack comprises at least two layers and has a thickness of at least 80 μm. More preferably, each stack comprises at least 10 layers and has a thickness of at least 400 μm, even more preferably each stack comprises at least 50 layers and has a thickness of at least 2 mm.

In various embodiments, each stack comprises at least two layers and has a thickness of at least 80 μm, wherein each layer has a thickness of about or at least 40 μm. More preferably, each stack comprises at least 10 layers and has a thickness of at least 400 μm, wherein each layer has a thickness of about or at least 40 μm. Even more preferably, each stack comprises at least 50 layers and has a thickness of at least 2 mm (2.000 μm), wherein each layer has a thickness of about or at least 40 μm.

Preferably, the method of generating a phantom/an imaging phantom as disclosed herein comprises generating stacks of multiple layers, wherein the multiple layers are glued layers. The step of gluing may comprise putting glue on one side of a layer and preferably spreading the glue evenly, followed by putting the next layer on the side of the layer carrying the glue.

In various embodiments of the methods disclosed herein, the weight ratio (% w/w) of ink composition:carrier is about 0.01-3:1, preferably the weight ratio (% w/w) of ink composition:carrier is about 0.1-3:1, more preferably the weight ratio (% w/w) of ink composition:carrier is about 1-3:1.

In various embodiments of the various aspects disclosed herein, the layer is a sheet. In other embodiments, the layer may be a fiber, e.g., a nonwoven fiber. In various embodiments, the layer comprises pulp material, preferably cellulose. Preferably, the layer material is composed of the elements H, C, and O. More preferably, the layer material is composed of the elements H, C, and O, and has a density of about 0.9 g/cm$^3$. In various embodiments, the layer material is composed of the elements H, C, and O, and has a density of about 0.9 g/cm$^3$, wherein the elemental composition of the base material is about 4-10% w/w H, about 45-55% w/w C, and about 40-46% w/w O, preferably about 6-8% w/w H, about 47-53% w/w C, and about 42-45% w/w O, more preferably about 7-8% w/w H, about 49-50% w/w C, and about 43-44% w/w O, and even more preferably about 7.2% w/w H, about 49.3% w/w C, and about 43.5% w/w O.

Preferably, the layer is a paper sheet. As described herein, it is preferred that the paper sheet is colorless, i.e., white.

In various embodiments, the paper may be paper with a grammage of 40-80 g/m$^2$, which is preferably coated on one side with a layer of low density polyethylene with a grammage of about 6-10 g/m$^2$. Preferably, the paper is a paper with a grammage of 50-70 g/m$^2$, which is preferably coated on one side with a layer of low density polyethylene with a grammage of about 7-9 g/m$^2$. More preferably, the paper is a paper with a grammage of about 60 g/m$^2$, which is preferably coated on one side with a layer of low density polyethylene with a grammage of about 8 g/m$^2$.

In various embodiments, all layers in one stack are of identical size and/or shape [prior to cutting]. In various embodiments, the layer has a size A0 (84.1×118.9 cm; 33.1×46.8 inches). In various other embodiments, the layer has a size A1 (59.4×84.1 cm; 23.4×33.1 inches). In various other embodiments, the layer has a size A2 (42.0×59.4 cm; 16.5×23.4 inches). In various other embodiments, the layer has a size A3 (29.7×42.0 cm; 11.7×16.5 inches). In still other embodiments, the layer has a size A4 (21.0×29.7 cm; 8.3×11.7 inches). Thus, the layer may have a size in the range of 21.0-84.1×29.7-118.9 cm (8.3-33.1×11.7-46.8 inches), without being limited thereto. In still other embodiments, the layer has a size A5 (14.8×21.0 cm; 5.8×8.3 inches). In still other embodiments, the layer has a size A6 (10.5×14.8 cm; 4.1×5.8 inches). Thus, the layer may even have a size in the range of 10.5-84.1×14.8-118.9 cm (4.1-33.1×5.8-46.8 inches), without being limited thereto.

As described herein, the layer (paper) stacking disclosed herein may comprise using one paper for each layer, i.e., there is no folding of individual or single layers. For example, it is preferred that the layer (paper) stacking disclosed herein does not comprise the folding of individual or single papers so that one paper makes 2 or 4 layers.

Furthermore, in various embodiments of the method of generating a phantom/an imaging phantom disclosed herein, the layer may advantageously comprise a thermoplastic coating, preferably a polyethylene coating, on one side of its surface. The thermoplastic coating on one side of the layer material needs to stick both to printed and non-printed carrier material. Furthermore, to prevent material degradation, the thermoplastic coating preferably molds at a temperature below 170° C., preferably at a temperature below 160° C., more preferably at temperature below 150° C., even more preferably at temperature below 140° C. In various embodiments, the thermoplastic coating molds at a temperature below 130° C.

Furthermore, in various embodiments of the method of generating a phantom/an imaging phantom disclosed herein, the weight ratio of layer material to thermoplastic coating is in the range between 1:1 to 20:1, preferably between 5:1 to 10:1. In various embodiments, the weight ratio of layer material to thermoplastic coating is in the range between 4:1 to 20:1, preferably between 4:1 to 10:1. Likewise, in various embodiments of the novel (imaging) phantom disclosed herein, the weight ratio of layer material to thermoplastic coating is in the range between 1:1 to 20:1, preferably between 5:1 to 10:1. In various embodiments, the weight ratio of layer material to thermoplastic coating is in the range between 4:1 to 20:1, preferably between 4:1 to 10:1.

In various embodiments, the method of generating a phantom/an imaging phantom disclosed herein comprises combining stacks, preferably stacks of glued layers, to generate an imaging phantom.

The chemical composition of all non-volatile compounds of the novel ink compositions is adjusted so that the printed phantom simulates a specific type of tissue or organ of a mammalian body, in particular a specific type of tissue or organ of a human or animal body. Accordingly, the term "phantom" or "imaging phantom" as used herein encompasses in particular soft/bone tissue (mimicking) phantoms, without, however, being limited thereto. This means that the term "phantom" or "imaging phantom" as used herein is to be understood to encompass phantoms mimicking parts of a body in general, or even a whole body. In various embodiments, the body is a human or animal body. In various other embodiments, the body is a mammalian body, including a human body, without being limited thereto. In various preferred embodiments, the mammalian body is a human body. In other embodiments, the animal body may be a body of any of fish, birds, insects, reptiles, and amphibians. As described elsewhere herein, the terms "imaging phantom", "phantom", "imaging model", and "phantom model" may be used interchangeably herein. The term "(imaging) phantom" encompasses both "anthropomorphic phantoms" and "animal phantoms". In preferred embodiments, the "phantom" or "imaging phantom" is an "anthropomorphic phantom". Accordingly, in preferred embodiments, the "phantom" or "imaging phantom" is an "anthropomorphic phantom", and the biological (soft/bone) tissue is human (soft/bone) tissue, and/or the biological (soft/bone) organ is a human (soft/bone) organ.

In various embodiments, the "phantom" or "imaging phantom" may be a "biological tissue phantom". In various embodiments, the terms "phantom"/"imaging phantom" and "biological (soft/bone) tissue phantom" or "biological (soft/bone) tissue mimicking phantom" may be used interchangeably herein. Here, the term "soft tissue (mimicking) phantom" includes muscles and organs. Thus, in various embodiments, the term "soft tissue (mimicking) phantom" means "phantom of/mimicking (human or animal) muscle tissue" or "(human or animal) organ (mimicking) phantom". In various embodiments, the (imaging) phantom or (human or animal) organ (mimicking) phantom provided by the present disclosure is a phantom of a (human or animal) lung, liver, kidney, brain, or intestine. In various embodiments, the (imaging) phantom or (human or animal) organ (mimicking) phantom provided by the present disclosure is a phantom of a (human or animal) tissue. Such an imaging phantom may be specifically considered as a tissue-equivalent (imaging) phantom. In various embodiments, the tissue-equivalent (imaging) phantom may be a phantom of the (human or animal) skin. As described herein, in various embodiments, "human or animal" means "mammalian". In various preferred embodiments, the tissue or organ is "human" tissue or organ.

In various other embodiments, the terms "phantom" or "imaging phantom" and "phantom of a human or animal body/human or animal body part" or "phantom mimicking a human or animal body/human or animal body part" may be used interchangeably herein. The term "human or animal body part" includes, e.g., the human or animal upper body (thorax), the head and a limb. Accordingly, in various embodiments, the (imaging) phantom provided by the present disclosure is a phantom of a human or animal upper body (thorax), i.e., a thorax (mimicking) phantom. In various other embodiments, the (imaging) phantom provided by the present disclosure is a phantom of a human or animal head. The (imaging) phantom provided by the present disclosure may be a phantom of the cortical bone, or may be a phantom of human or animal muscles, preferably human or animal skeletal muscle. In various embodiments, the term "human or animal body part" also includes human or animal organs, preferably human or animal lung, liver, kidney, brain, or intestine. In various embodiments, "human or animal" means "mammalian". In various embodiments, "human" (tissue/body/body part/organ) is preferred. As further described herein, the present disclosure encompasses (imaging) phantoms not only for use in 3D imaging, but also for use in 2D imaging. Accordingly, in various embodiments, the novel (imaging) phantoms disclosed herein may be considered 2D and/or 3D (imaging) phantoms. As further described herein, the term "imaging" (or "medical imaging") includes various radiological imaging techniques, including, but not limited to, X-ray radiography, fluoroscopy, magnetic resonance imaging (MRI), and the like.

The term "mimicking" specifically means mimicking a biological tissue or organ with respect to its radiation absorption characteristics (or radiation absorbing properties), while also showing the anatomy of the respective tissue or organ. Thus, the terms "soft/bone tissue phantom" or "soft/bone tissue mimicking phantom" specifically mean a phantom mimicking the radiation absorbing properties (or radiation absorption characteristics) of a biological soft and/or bone tissue. The phantom is thereby mimicking the biological soft and/or bone tissue in equivalent form with respect to the radiation absorbing properties. Also, the phantom shows the anatomy of the corresponding biological soft and/or bone tissue.

Likewise, the terms "phantom of a human or animal body/human body part" or "phantom mimicking a human or animal body/human body part" specifically mean a phantom mimicking the radiation absorbing properties (or radiation absorption characteristics) of the human or animal body or a part of a human or animal body. The phantom is thereby mimicking the (part of the) human or animal body in equivalent form with respect to the radiation absorbing properties. Also, the phantom shows the anatomy of the corresponding human or animal body or part thereof. In various embodiments, "human or animal" means "mammalian". In various embodiments, "human" (body/body part) is preferred.

In various embodiments of the present disclosure, a novel (imaging) phantom as disclosed herein is mimicking (all types of) biological tissue or organ with a density greater than 0.9 g/cm³ (cf. Table 1), more preferably greater than 0.93 g/cm³. Preferably, the novel (imaging) phantom is mimicking (all types of) biological tissue or biological organ with a density greater than 1.0 g/cm³ (cf. Table 1), more preferably greater than 1.04 g/cm³. In various embodiments, the novel (imaging) phantom is mimicking (all types of) biological tissue or biological organ with a density in the range of 0.9 g/cm³ to 2.0 g/cm³, preferably in the range of 1.0 g/cm³ up to (and including) 1.92 g/cm³ (cf. Table 1). In various other embodiments, the novel (imaging) phantom is mimicking (all types of) biological soft tissue or biological organ with a density in the range of 0.9 g/cm³ to 1.2 g/cm³, preferably in the range of 0.94 g/cm³ up to (and including) 1.2 g/cm³ (cf. Table 1). In still other embodiments, the novel (imaging) phantom is mimicking (all types of) biological bone tissue or biological organ with a density in the range of 0.9 g/cm³ to 1.95 g/cm³, preferably in the range of 0.94 g/cm³ up to (and including) 1.95 g/cm³ (cf. Table 1).

The novel ink compositions provided by the present disclosure may contain one or more additives. Preferably, such additives are present in the compositions in an amount of less than 20% w/w, preferably less than 10% w/w, more preferably less than 5% w/w relative to the total dry weight of the components dissolved in the ink composition.

In various embodiments, the "ink composition" disclosed herein may be described as a "radiopaque ink composition", in accordance with the special technical effect provided for by the comprised radiation absorbing molecules and/or salts.

The terms "ink composition" and "ink" or "ink formulation" may be used herein interchangeably.

EXAMPLES

Tissue Equivalent Phantoms

Physical Background—Radiation Absorption

Following the Lambert-Beer law, radiation absorption properties of a material depend on the materials thickness, mass attenuation coefficient $\mu/\rho$ and physical density $\rho$.

$$I = I_0 e^{-\frac{\mu}{\rho}\rho d} \qquad \text{Equation 1}$$

Lambert-Beer law, $I$-radiation intensity, $I_0$-initial radiation intensity, $\mu/\rho$-mass attenuation cofficient, $\rho$-density, $d$-material thickness.

The mass attenuation coefficient of a material depends on its chemical composition and on the energy of the incident radiation. While low energy radiation is applied in planar x-ray imaging (20-120 keV) and computed tomography (80-140 keV), higher photon energies are used in radiation therapy. Common radiotherapy devices operate in the photon energy area of up to 20 MeV, but for special applications energy levels up to 250 MeV exist. FIG. 1 shows the photon energy range in CT and RT.

The mass attenuation coefficient seems to be influenced by the atomic number of an element, as shown in FIG. 2 on the example of oxygen, calcium and iodine. Elements with higher atomic number have absorption edges within the photon energy range employed in CT and RT, which leads to discontinuous absorption behavior.

Elements with high atomic number possess strong radiation attenuation properties, but are not suitable as radiation absorbers for the creation of tissue equivalent phantoms, which realistically simulate the radiation absorption properties of human tissue over the energy range relevant for CT and RT. Suitable phantom materials must reproduce the chemical composition and physical density of human tissue.

Composition of Biological (Human) Tissue

The basis for the calculation of phantom materials are chemical composition and density values for different types of biological (in particular human) tissue. Adipose tissue is mostly composed of elements with a low atomic number and has a density in the range of 0.9-0.97 g/cm³. Soft tissue such as muscles or organs are similarly composed of elements with a low atomic number, but have compared to adipose tissue a higher oxygen and a lower carbon content. Their physical density is in the range of 1.0-1.1 g/cm³. Bone tissue contains besides low atomic number elements a significant amount of phosphorus and calcium and has density values of up to 1.92 g/cm³.

TABLE 1

Elemental composition and density values of selected human tissues (according to White and Woodard 1986, *The British Journal of Radiology* 59: 1209-1219)

| Tissue | Elemental composition (w/% w/w) | | | | | | | | | | | Density | |
|---|---|---|---|---|---|---|---|---|---|---|---|---|---|
| | H | C | N | O | Na | P | S | Cl | K | Ca | Fe | g/cm³ | el.m⁻³ *10²⁶ |
| Fat | 11.6 | 68.1 | 0.2 | 19.8 | 0.1 | | 0.1 | 0.1 | | | | 0.93 | 3118 |
| Pancreas | 10.6 | 16.9 | 2.2 | 69.4 | 0.2 | 0.2 | 0.1 | 0.2 | 0.2 | | | 1.04 | 3457 |
| Muscle | 10.1 | 17.1 | 3.6 | 68.1 | 0.1 | 0.2 | 0.3 | 0.1 | 0.4 | | | 1.05 | 3475 |
| Liver | 10.2 | 13.9 | 3.0 | 71.6 | 0.2 | 0.3 | 0.3 | 0.2 | 0.3 | | | 1.06 | 3511 |
| Spongiosa | 8.5 | 40.4 | 2.8 | 36.7 | 0.1 | 3.4 | 0.2 | 0.2 | 0.1 | 7.4 | 0.1 | 1.18 | 3844 |
| Cortical Bone | 3.4 | 15.5 | 4.2 | 43.5 | 0.1 | 10.3 | 0.3 | | | 22.5 | | 1.92 | 5952 |

The different compositions and density values of human tissues are reflected in their CT values (FIG. 3). CT devices are calibrated to air and water, with water having a CT value of 0 Hounsfield units (HU) and air −1000 HU. With increasing photon energy from 80 to 135 keV, human soft tissue has almost constant to slightly increasing CT values in the range of approximately −100-+100 HU. Bone tissue in contrast displays higher CT values of up to +1400 HU that are decreasing with increasing photon energy.

Phantom Manufacturing Technique

Starting from a standard patient CT scan, the grey scale encoded CT data set is processed into printable data. Radiopaque printing is carried out using thermal inkjet technology to print the processed CT images to a phantom base material using water-based radiopaque inks with printing resolution of up to 600 dpi. As base material, paper with a special chemical composition is used. The paper is coated on one side with a thin layer of a thermoplastic to allow temperature controlled agglutination of the single papers. Thin stacks of paper are glued together and cutted to outer and inner contours using a laser cutter. In a further step, the stacks are put together to build the complete phantom. Such a phantom manufacturing process is exemplified in FIG. 4.

Phantom Material Requirements

The manufacturing process leads to specific material requirements. The phantom base material will be used to simulate all types of human tissue with a density greater than 0.9 g/cm³. It needs basic radiation absorption properties that can be adjusted to the desired values by adding specifically radiation absorbing materials. Therefore, it is composed of elements with a low atomic number and adjusted to a density of 0.9 g/cm³ and a CT value of around −120 HU at a tube voltage of 120 kVp. The base material is comprised of a carrier material and a thermoplastic coating. To allow radiopaque printing of CT images, the carrier material needs to be processable in thin sheets with a thickness of approx. 0.05-0.2 mm, have a sufficient tensile strength and needs to be able to absorb aqueous ink solutions without losing the high resolution of the printed images. In addition, the carrier material needs to be able to absorb large amounts of ink so that its density reaches a value of up to 1.92 g/cm³ (maximum bone density in the human body).

The thermoplastic coating on one side of the carrier material needs to stick both to printed and non-printed carrier material and mold at a temperature below 130° C. to prevent material degradation. Weight ratio of carrier material to thermoplastic coating should be in the range of 4:1-20:1.

Biological tissue will be simulated by printing different radiopaque inks on the phantom base material. The absorption characteristics of the phantom are therefore resulting out of the combination of base material and non-volatile contents of the radiopaque inks that remain absorbed in the carrier material after evaporation of all volatile ink compounds.

The inks required for the simulation of biological tissue can be categorized into two basic types: "Soft tissue inks" used for the simulation of biological soft tissue, and "bone tissue inks" used for the simulation of biological bone tissue. While soft tissue inks are comprised mostly out of compounds with elements with a low atomic number in the range of Z=1-11, bone tissue inks contain a specific amount of elements with an atomic number in the range of Z=13-22.

The specific chemical composition of radiopaque inks is adjusted by calculating mass attenuation coefficients of the target biological tissue and the ink composition, or the combination of ink composition and phantom base material, respectively. Mass attenuation coefficients for the elements can be obtained from their atomic cross-sections, where tabulated values can be found in literature. Mass attenuation coefficients for compounds and mixtures are calculated as weighted average from their elemental composition.

$$\frac{\mu}{\rho} = \frac{\sigma_a}{N_A \sum_i \frac{w_i}{A_i}}$$

$$\mu_\rho = \sum_i w_i \left(\frac{\mu}{\rho}\right)_i$$

Equation 2 and 3

Calculation of mass attenuation coefficients, $\mu/\rho$- mass attenuation coefficient, $\sigma_a$- atomic cross section, $N_A$- Avogadro's number, $A_i$- atomic weight, $w_i$- fractional weight Different types of biological tissue can be simulated by formulating different ink compositions and/or by combining different amounts of one or multiple inks with the phantom basis material. The ratio of ink to phantom base material is thereby calculated from the density of the target biological tissue. To simulate all types of biological soft tissue, the combination of soft tissue ink and phantom base material needs to cover a density range from 0.9 to approximately 1.2 g/cm³ and a CT value range from −120 to +150 HU. For the simulation of biological bone tissue, the combination of bone tissue ink and phantom base material needs to cover a density range from 0.9 to approximately 1.95 g/cm³ and a CT value range from −120 to +1400 HU.

Cavities or tissue with densities below 0.9 g/cm³ are simulated by using cut outs, perforations or by placing insets of foamed plastic into the phantom. All used materials need to be stable, not corrosive or aggressive towards any utilized materials, not toxic and should have no or only moderate hygroscopy.

TABLE 2

Phantom material target values

| Material | Simulated tissue | HU/120 kVp | Density [g/cm³] |
|---|---|---|---|
| Phantom base material | | −120 | 0.9 |
| Base material + soft tissue ink | Human soft tissue | −120-+150 | 0.9-1.2 |
| Base material + Bone tissue ink | Human bone tissue | −120-+1400 | 0.9-1.95 |
| Cuttings, Perforations, foamed plastic inserts | Cavities, lung tissue | −1000-0 | <0.9 |

Phantom Base Material

A phantom base material that fulfills all requirements is a kraft paper with a grammage of 60 g/m², which is coated on one side with a layer of low density polyethylene with a grammage of 8 g/m². The material only consists of hydrogen, carbon and oxygen with a composition given in Table 3. The polyethylene firmly sticks to the kraft paper. Stacking of the base material to three-dimensional objects is carried out by pressing the sheets together at a temperature of 110° C., whereby the polyethylene molds and firmly glues the sheets together. The applied pressure is adjusted so that the final phantom material has a density of 0.9 g/cm³.

TABLE 3

Elemental composition and density of phantom base material

| | Elemental composition (% w/w) | | | Density |
|---|---|---|---|---|
| Material | H | C | O | [g/cm³] |
| Phantom base material | 7.2 | 49.3 | 43.5 | 0.9 |

Mass attenuation coefficients were calculated for an energy range of 0.01-100 MeV. A sample of the material was examined in CT. The resulting material has a CT value of −120 HU at a tube voltage of 120 kVP. With increasing tube voltage from 80 to 140 kVp, the CT values are slightly increasing (FIG. 5).

Example 1: Skeletal Muscle Phantom

As an example for a soft tissue phantom, skeletal muscle tissue was chosen as reference material. The chemical composition and density values for skeletal muscle tissue were taken from the literature (D. R. White, H. Q. Woodard, *The British Journal of Radiology* 1986, 59, 1209-1219). On the basis of these values, the mass attenuation coefficient of the tissue was calculated for an energy range of 0.01-100 MeV. The required ratio of ink to base material was calculated so that the finished phantom has the same density as the reference tissue. An ink composition was formulated, so that the mass attenuation coefficient of a phantom manufactured by printing a defined amount of this ink on the phantom base material closely matches the one of the reference tissue.

Exemplary ink formulation for "skeletal muscle ink": Urea (25.0 g), L-proline (8.0 g), sodium chloride (10.5 g), saccharose (4.0 g), IGEPAL-Co-630 (0.1 g), tributyl phosphate (0.1 g), benzisothiazolinone (0.08 g), malachite green oxalate (0.015 g), 2-propanol (1.25 g) and 2-pyrrolidon (1.25 g) were dissolved in distilled water. Distilled water is added until the solution has a volume of 50.0 mL at ambient conditions.

TABLE 4

Elemental composition of skeletal muscle ink

| | Elemental composition (% w/w) | | | | | | | |
|---|---|---|---|---|---|---|---|---|
| Material | H | C | N | O | Na | P | S | Cl | K |
| Non-volatile ink components | 5.4 | 23.1 | 26.5 | 23.0 | 8.6 | | 0.1 | 13.3 | |

The ink was printed on the phantom base material. The resulting phantom consisted of 86% w/w phantom base material and 14% w/w non-volatile ink components. Elemental composition of tissue and phantom is given in Table 5.

TABLE 5

Elemental composition and density of skeletal muscle tissue and phantom

| | Elemental composition (% w/w) | | | | | | | | | Density |
|---|---|---|---|---|---|---|---|---|---|---|
| Material | H | C | N | O | Na | P | S | Cl | K | [g/cm³] |
| Skeletal muscle tissue | 10.1 | 17.1 | 3.6 | 68.1 | 0.1 | 0.2 | 0.3 | 0.1 | 0.4 | 1.05 |
| Skeletal muscle phantom | 7.1 | 43.9 | 3.8 | 42.1 | 1.2 | | | 1.9 | | 1.05 |

The mass attenuation coefficients of tissue and phantom are closely matching, with a maximum deviation of 3.5% in the relevant energy range of 0.02-100 MeV (FIG. 6).

Example 2: Cortical Bone Phantom

Following the same procedure as described above, a phantom mimicking cortical bone tissue was created.

Ink formulation for "cortical bone ink": L-proline (1.84 g), saccharose (3.07 g), potassium chloride (13.0 g), Eos in B (0.02 g) and 2-pyrrolidone (2.50 g) were dissolved in distilled water. Distilled water is added until the solution has a volume of 50.0 mL at ambient conditions.

TABLE 6

Elemental composition of cortical bone ink

| Material | Elemental composition (% w/w) | | | | | | | | |
|---|---|---|---|---|---|---|---|---|---|
| | H | C | N | O | Na | P | S | Cl | K |
| Non-volatile ink components | 1.9 | 12.8 | 1.3 | 11.7 | | | 0.1 | 34.3 | 37.9 |

The ink was printed on the phantom base material. The resulting phantom consisted of 46.9% w/w phantom base material and 53.1% w/w non-volatile ink components. Elemental composition of tissue and phantom is given in Table 7.

TABLE 7

Elemental composition and density of cortical bone tissue and phantom

| Material | Elemental composition (% w/w) | | | | | | | | | | | Density [g/cm³] |
|---|---|---|---|---|---|---|---|---|---|---|---|---|
| | H | C | N | O | Na | Mg | P | S | Cl | K | Ca | |
| Cortical bone tissue | 3.4 | 15.5 | 4.2 | 43.5 | 0.1 | 0.2 | 10.3 | 0.3 | | | 22.5 | 1.92 |
| Cortical bone phantom | 4.5 | 28.9 | 0.7 | 27.5 | | | | | 18.3 | 20.2 | | 1.92 |

The mass attenuation coefficients of tissue and phantom are closely matching, with a maximum deviation of 1.0% in the relevant energy range of 0.02-100 MeV (FIG. 7—the graphs for the cortical bone phantom and cortical bone are actually lying on top of each other).

Figure 8:
FIG. 8: provides a table showing mass attenuation coefficients and density values of phantoms and reference materials.

FIG. 8 shows mass attenuation coefficients and density values of exemplary phantoms and reference materials.

The invention claimed is:

1. An ink composition conferring radiation-absorbing properties mimicking bone tissue, wherein the ink composition comprises dissolved radiation-absorbing molecules, the radiation-absorbing molecules composed of chemical elements, wherein each chemical element has an atomic number Z which is:
   an atomic number in the range Z=1–22, wherein the radiation-absorbing molecules comprise a radiation-absorbing salt selected from the group consisting of: phosphate salts,
   and a combination of any two or more phosphate salts
   wherein the radiation-absorbing phosphate salt or phosphate salts are water-soluble, non-volatile compounds having a boiling point ≥200° C., and wherein the ink composition has a viscosity in the range between 1-30 millipascal-second (mPa·s).

2. The ink composition of claim 1, wherein the radiation-absorbing phosphate salts composed of elements having an atomic number in the range Z=1–22 are present in the composition in an amount of at least 50% weight/weight (w/w), relative to a total dry weight of the dissolved radiation-absorbing molecules.

3. The ink composition of claim 2, wherein a remaining amount of 50% w/w or less, or 30% w/w or less, respectively, relative to the total dry weight of the dissolved radiation-absorbing molecules comprises radiation-absorbing organic molecules and/or radiation-absorbing salts composed of elements having a low-atomic number 1≤Z≤11, and/or wherein an amount of radiation-absorbing molecules composed of elements having an atomic number Z>22 present in the composition does not exceed 5% w/w relative to the total dry weight of the dissolved radiation-absorbing molecules.

4. An imaging phantom exhibiting radiation-absorbing properties mimicking biological tissue at a photon energy in the range of 20 keV to 100 MeV, wherein the phantom is built up of layers comprising:
   (i) the radiation-absorbing molecules of the ink composition according to claim 1.

5. The imaging phantom according to claim 4, wherein the phantom shows a mass attenuation coefficient μ/ρ value≤0.2 cm²/g at 100 keV.

6. The imaging phantom according to claim 4, wherein the phantom:
   (i) mimics the radiation-absorbing properties of biological soft tissue; and/or has a Hounsfield Unit (HU) value between −200 and +300 in a CT scan with a tube voltage of 120 kV; and/or
   (ii) mimics the radiation-absorbing properties of biological bone tissue, preferably of cortical bone tissue; and/or has a Hounsfield Unit (HU) value between −50 and +3000 in a CT scan with a tube voltage of 120 kV.

7. The imaging phantom according to claim 4, wherein each of the layers has a thickness of at least 40 μm, and/or comprises pulp material, and/or comprises a thermoplastic coating, on one surface.

8. The imaging phantom according to claim 4, wherein the phantom shows a mass attenuation coefficient μ/ρ value in the range of 0.160-0.195 cm²/g at 100 keV.

9. A method of generating an imaging phantom exhibiting radiation-absorbing properties mimicking biological tissue, wherein the method comprises a step of printing the ink composition according to claim 1 onto multiple layers.

10. The method of claim 9, further comprising generating stacks of multiple layers.

11. The ink composition of claim 1, wherein the ink composition has a viscosity in the range between 2-15 millipascal-second (mPa·s).

12. The ink composition of claim 1, wherein the phosphate salt or phosphate salts are selected from the group consisting of: diphosphates, triphosphates, polyphosphates, hydrogenphosphates, dihydrogenphosphates, monothiophosphates, dithiophosphates, trithiophosphates, tetrathiophosphates; phosphonates, phosphinates, and a combination of any two or more thereof.

13. The ink composition of claim 1, wherein the radiation-absorbing molecules confer to an imaging phantom, which is generated with the ink composition, a mass attenuation coefficient $\mu/\rho$ value in the range of 0.160-0.195 cm$^2$/g at 100 keV.

* * * * *